United States Patent
Ku et al.

(10) Patent No.: US 7,393,941 B2
(45) Date of Patent: Jul. 1, 2008

(54) MXA AS AN ANTIVIRAL DRUG AND AS A TARGET FOR IDENTIFICATION OF ANTIVIRAL DRUGS FOR DNA VIRUS INFECTIONS

(75) Inventors: Chia-Chi Ku, Mountain View, CA (US); Ann M. Arvin, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/486,901

(22) Filed: Jul. 13, 2006

(65) Prior Publication Data

US 2007/0218466 A1  Sep. 20, 2007

Related U.S. Application Data

(60) Provisional application No. 60/784,277, filed on Mar. 20, 2006.

(51) Int. Cl.
| | |
|---|---|
| *C07H 21/04* | (2006.01) |
| *A61K 8/00* | (2006.01) |
| *A61K 39/395* | (2006.01) |
| *C12P 21/06* | (2006.01) |
| *C12N 1/12* | (2006.01) |
| *C12N 15/00* | (2006.01) |
| *C12N 5/00* | (2006.01) |
| *A61K 39/02* | (2006.01) |
| *C12Q 1/68* | (2006.01) |
| *C12Q 33/53* | (2006.01) |

(52) U.S. Cl. ............... 536/23.1; 424/130.1; 424/70.1; 435/69.1; 435/252.3; 435/320.1; 435/325

(58) Field of Classification Search .................. None
See application file for complete search history.

(56) References Cited

U.S. PATENT DOCUMENTS

2004/0209800 A1 * 10/2004 Mushinski et al. ............ 514/12

OTHER PUBLICATIONS

Horisberger et al., Interferon-Induced Human Protein MxA Is a GTPase Which Binds Transiently to Cellular Proteins, 1992, Journal of Virology, vol. 66, No. 8, pp. 4705-4709.*
Fernandez et al., Hepatitis B virus downregulates the human interferon-inducible MxA promoter through direct interaction of precore/core proteins, 2003, Journal of General Virology, vol. 84, pp. 2073-2082.*

(Continued)

*Primary Examiner*—Bruce Campell
*Assistant Examiner*—Benjamin P. Blumel
(74) *Attorney, Agent, or Firm*—Paula A. Borden; Carol L. Francis; Bozicevic, Field & Francis LLP

(57) ABSTRACT

The invention features methods and compositions for use in a screening assay to identify agents having antiviral activity against a DNA virus by assessing the effect of a candidate agent upon alternative splicing of MxA, or by assessing the effect of a candidate agent on production of a variant form of MxA protein. The invention also provides methods for enhancing resistance of cells to infection by a DNA virus by providing for elevated MxA and/or by providing for reduced production of variant MxA protein.

13 Claims, 28 Drawing Sheets
(8 of 28 Drawing Sheet(s) Filed in Color)

OTHER PUBLICATIONS

Asano et al., Polymorphisms and the Antiviral Property of Mx1 protein, 2002, Journal of Veterinary Medican Science, vol. 64, No. 12, pp. 1085-1089.*

Aebi et al., "cDNA Structures and Regulation of Two Interferon-Induced Human Mx Proteins", (1989), Moleular and Cellular Biology, vol. 9, No. 11, pp. 5062-5072.

Barreca et al., "Suppression of herpes simplex virus I in MDBK cells via the interferon pathway", (2004), Journal of Virology, vol. 78, No. 16, pp. 8641-8653.

Flohr et al., "The central interactive region of human MxA GTPase is involved in GTPase activation and interaction with viral target structures", (1999) Federation of European Biochemical Society, Letters 463, pp. 24-28.

Gordien et al., "Inhibition of Hepatitis B Virus Replication by the Interferon-Inducible MxA Protein", (2001), Journal of Virology, vol. 75, No. 6, pp. 2684-2691.

Jatiani et al., "Expression of the antiviral protein MxA in cells transiently pertubs endocutosis"(2004), Biochemical and Biophysical Research Communications, vol. 323, pp. 541-546.

Mossman et al., "Herpes Simplex virus triggers and then disarms a host antiviral response", (2001), Journal of Virology, vol. 75, No. 2, pp. 750-758.

Noisakran et al. "Type I interferons and herpes simplex virus infection: a naked DNA approach as a therapeutic option", (2001), Immunol Research, vol. 24, No. 1, pp. 1-11.

Punda-Polic ET al. "Synergistic anti varicella-zosater virus activity of interferon-alpha 2a and acyclovir in corneal cells", (1999), Zentralblatt fur Bakteriologie, vol. 289, No. 2, pp. 203-210.

* cited by examiner

FIG. 9A

Full-length MxA coding sequence

```
   1 ccacgcgtcc gcccagtgtc acggtggaca cgcctccctc gcgcccttgc cgcccacctg
  61 ctcacccagc tcagggqctt tggaattctg tggccacact gcgaggagat cggttctggg
 121 tcggaggcta caggaagact cccactccct gaaatctgga gtgaagaacg ccgccatcca
 181 gccaccattc aaggaggtg caggagaaca gctctgtgat accatttaac ttgttgacat
 241 tacttttatt tgaaggaacg tatattagag cttactttgc aaagaaggaa gatggttgtt
 301 tccgaagtgg acatcgcaaa agctgatcca gctgctgcat cccaccctct attactgaat
 361 ggagatgcta ctgtggccca gaaaaatcca ggctcggtgg ctgagaacaa cctgtgcagc
 421 cagtatgagg agaaggtgcg cccctgcatc gacctcattg actccctgcg ggctctaggt
 481 gtggagcagg acctggccct gcagccatc gccgtcatcg gggaccagag ctcgggcaag
 541 agctccgtgt tggaggcact gtcaggagtt gcccttccca gaggcagcgg gatcgtgacc
 601 agatgcccgc tggtgctgaa actgaagaaa cttgtgaacg aagataagtg gagaggcaag
 661 gtcagttacc aggactacga gattgagatt cggatgcttc agaggtaga aaggaaatt
 721 aataaagccc agaatgccat cgccggggaa ggaatgggaa tcagtcatga gctaatcacc
 781 ctggagatca gctcccgaga tgtcccggat ctgactctaa tagaccttcc tggcataacc
 841 agagtggctg tgggcaatca gcctgctgac attgggtata agatcaagac actcatcaag
 901 aagtacatcc agaggcagga gacaatcagc ctggtggtgg tccccagtaa tgtggacatt
 961 gccaccacag aggctctcag catggcccag gaggtggacc ccgagggaga caggaccatc
1021 ggaatcttga cgaagcctga tctggtggac aaaggaactg aagacaaggt tgtggacgtg
1081 gtgcggaacc tcgtgttcca cctgaagaag ggttacatga ttgtcaagtg ccggggccag
1141 caggagatcc aggaccagct gagcctgtcc gaagccctgc agagagagaa gatcttcttt
1201 gagaaccacc catatttcag ggatctgctg gaggaaggaa aggccacggt tcctgcctg
1261 gcagaaaaac ttaccagcga gctcatcaca catatctgta atctctgcc cctgttagaa
1321 aatcaaatca aggagactca ccagagaata acagaggagc tacaaaagta tggtgtcgac
1381 ataccggaag acgaaaatga aaaaatgttc ttcctgatag ataaaattaa tgcctttaat
1441 caggacatca ctgctctcat gcaaggagag gaaactgtag gggaggaaga cattcggctg
1501 tttaccagac tccgacacga gttccacaaa tggagtacaa taattgaaaa caattttcaa
     Ex14
1561 gaaggccata aaattttgag tagaaaaatc cagaaatttg aaaatcagta tcgtggtaga
1621 gagctgccag gctttgtgaa ttacaggaca tttgagacaa tcgtgaaaca gcaaatcaag
1681 gcactggaag agccggctgt ggatatgcta cacaccgtga cggatatggt ccggcttgct
1741 ttcacagatg tttcgataaa aaattttgaa gagttttta acctccacag aaccgccaag
1801 tccaaaattg aagacattag agcagaacaa gagagagaag gtgagaagct gatccgcctc
1861 cacttccaga tggaacagat tgtctactgc caggaccagg tatacagggg tgcattgcag
1921 aaggtcagag agaaggagct ggaagaagaa agaagaaga atcctggga ttttggggct
1981 ttccaatcca gctcggcaac agactcttcc atggaggaga tctttcagca cctgatggcc
     Ex17
2041 tatcaccagg aggccagcaa gcgcatctcc agccacatcc ctttgatcat ccagttcttc
2101 atgctccaga cgtacggcca gcagcttcag aaggccatgc tgcagctcct gcaggacaag
2161 gacacctaca gctggctcct gaaggagcgg agcgacacca gcgacaagcg gaagttcctg
2221 aaggagcggc ttgcacggct gacgcaggct cggcgccggc ttgccagtt ccccggttaa
2281 ccacactctg tccagccccg tagacgtgca cgcacactgt ctgccccgt tcccgggtag
2341 ccactggact gacgacttga gtgctcagta gtcagactgg atagtccgtc tctgcttatc
```

FIG. 9B

```
2401 cgttagccgt ggtgatttag caggaagctg tgagagcagt ttggtttcta gcatgaagac
2461 agagccccac cctcagatgc acatgagctg gcgggattga aggatgctgt cttcgtactg
2521 ggaaagggat tttcagccct cagaatcgct ccaccttgca gctctcccct tctctgtatt
2581 cctagaaact gacacatgct gaacatcaca gcttatttcc tcatttttat aatgtccctt
2641 cacaaaccca gtgttttagg agcatgagtg ccgtgtgtgt gcgtcctgtc ggagccctgt
2701 ctcctctctc tgtaataaac tcatttctag cagacaaaaa aaaaaaaaa aaa
```

FIG. 9C variant MxA coding sequence

```
   1 ccacgcgtcc gcccagtgtc acggtggaca cgcctccctc gcgcccttgc cgcccacctg
  61 ctcacccagc tcagggcttt tggaattctg tggccacact gcgaggagat cggttctggg
 121 tcggaggcta caggaagact cccactccct gaaatctgga gtgaagaacg ccgccatcca
 181 gccaccattc caaggaggtg caggagaaca gctctgtgat accatttaac ttgttgacat
 241 tacttttatt tgaaggaacg tatattagag cttactttgc aaagaaggaa gatggttgtt
 301 tccgaagtgg acatcgcaaa agctgatcca gctgctgcat cccaccctct attactgaat
 361 ggagatgcta ctgtggccca gaaaaatcca ggctcggtgg ctgagaacaa cctgtgcagc
 421 cagtatgagg agaaggtgcg cccctgcatc gacctcattg actccctgcg ggctctaggt
 481 gtggagcagg acctggccct gccagccatc gccgtcatcg ggaccagag ctcgggcaag
 541 agctccgtgt tggaggcact gtcaggagtt gcccttccca gaggcagcgg gatcgtgacc
 601 agatgcccgc tggtgctgaa actgaagaaa cttgtgaacg aagataagtg gagaggcaag
 661 gtcagttacc aggactacga gattgagatt tcggatgctt cagaggtaga aaaggaaatt
 721 aataaagccc agaatgccat cgccggggaa ggaatgggaa tcagtcatga gctaatcacc
 781 ctggagatca gctcccgaga tgtcccggat ctgactctaa tagaccttcc tggcataacc
 841 agagtggctg tgggcaatca gcctgctgac attgggtata agatcaagac actcatcaag
 901 aagtacatcc agaggcagga gacaatcagc ctggtggtgg tccccagtaa tgtggacatt
 961 gccaccacag aggctctcag catggcccag gaggtggacc ccgagggaga caggaccatc
1021 ggaatcttga cgaagcctga tctggtggac aaaggaactg aagacaaggt tgtggacgtg
1081 gtgcggaacc tcgtgttcca cctgaagaag ggttacatga ttgtcaagtg ccggggccag
1141 caggagatcc aggaccagct gagcctgtcc gaagccctgc agagagagaa gatcttcttt
1201 gagaaccacc catatttcag ggatctgctg gaggaaggaa aggccacggt tccctgcctg
1261 gcagaaaaac ttaccagcga gctcatcaca catatctgta aatctctgcc cctgttagaa
1321 aatcaaatca aggagactca ccagagaata acagaggagc tacaaaagta tggtgtcgac
1381 ataccggaag acgaaaatga aaaaatgttc ttcctgatag ataaaattaa tgcctttaat
1441 caggacatca ctgctctcat gcaaggagag gaaactgtag gggaggaaga cattcggctg
1501 tttaccagac tccgacacga gttccacaaa tggagtacaa taattgaaaa caattttcaa
     (Ex14-16)
1561 gaag
         Ex17
1565     g aggccagcaa gcgcatctcc agccacatcc ctttgatcat ccagttcttc
1616 atgctccaga cgtacggcca gcagcttcag aaggccatgc tgcagctcct gcaggacaag
1676 gacacctaca gctggctcct gaaggagcgg agcgacacca gcgacaagcg gaagttcctg
1736 aaggagcggc ttgcacggct gacgcaggct cggcgccggc ttgcccagtt ccccggttaa
1796 ccacactctg tccagccccg tagacgtgca cgcacactgt ctgccccgt tcccgggtag
1856 ccactggact gacgacttga gtgctcagta gtcagactgg atagtccgtc tctgcttatc
1916 cgttagccgt ggtgatttag caggaagctg tgagagcagt ttggtttcta gcatgaagac
1976 agagccccac cctcagatgc acatgagctg gcgggattga aggatgctgt cttcgtactg
2036 ggaaagggat tttcagccct cagaatcgct ccaccttgca gctctcccct tctctgtatt
2096 cctagaaact gacacatgct gaacatcaca gcttatttcc tcattttat aatgtccctt
2156 cacaaaccca gtgttttagg agcatgagtg ccgtgtgtgt gcgtcctgtc ggagccctgt
2216 ctcctctctc tgtaataaac tcatttctag cagacaaaaa aaaaaaaaa aaa
```

FIG. 10A

```
                                                            938
MxA    ..............   ..............   ..............   ......GT G GTC CCC AGT
viMxA  NGNNNTTAGC ATTGATTAGC GGCCGCGAAT TCGCCCTTGT G GTC CCC AGT
                                                            V   P   S

MxA    AAT GTG GAC ATT GCC ACC ACA GAG GCT CTC AGC ATG GCC CAG GAG GTG GAC
viMxA  AAT GTG GAC ATC GCC ACC ACA GAG GCT CTC AGC ATG GCC CAG GAG GTG GAC
       N   V   D   I   A   T   T   E   A   L   S   M   A   Q   E   V   D

MxA    CCC GAG GGA GAC AGG ACC ATC GGA ATC TTG ACG AAG CCT GAT CTG GTG GAC
viMxA  CCC GAG GGA GAC AGG ACC ATC GGA ATC TTG ACG AAG CCT GAT CTG GTG GAC
       P   E   G   D   R   T   I   G   I   L   T   K   P   D   L   V   D

MxA    AAA GGA ACT GAA GAC GAC AAG GTT GTG GAC GTT GTG CGG TGC CGG GGC CAC
viMxA  AAA GGA ACT GAA GAC GAC AAG GTT GTG GAC GTT GTG CGG TGC CGG GGC CAC
       K   G   T   E   D   D   K   V   V   D   V   V   R   C   R   G   H

MxA    CTG AAG AAG GGT TAC ATG ATT GTC AAG GCC CTG CTG GAG CAG AAG ATC CAG
viMxA  CTG AAG AAG GGT TAC ATG ATT GTC AAG GCC CTG CTG GAG CAG AAG ATC CAG
       L   K   K   G   Y   M   I   V   K   A   L   L   E   Q   K   I   Q

MxA    GAC CAG AGC CTG AGC CTG TCC GAA GCC CTG CTG CTG GAG GAA AGA GAG GAG
viMxA  GAC CAG AGC CTG AGC CTG TCC GAA GCC CTG CTG CTG GAG GAA AGA GAG GAG
       D   Q   L   S   L   S   E   A   L   L   L   E   E   R   E   E

MxA    AAC CAC CCA TAT TTC AGG GAT CTT ACC AGC GAG CTC ATC AAG GGA AAG GCC
viMxA  AAC CAC CCA TAT TTC AGG GAT CTT ACC AGC GAG CTC ATC AAG GGA AAG GCC
       N   H   P   Y   F   R   D   L   T   S   E   L   I   K   G   K   A

MxA    TGC TGC CTG CTG GCA GAA AAA CTT GAA AAT CAA ATC ATC ACA CAT ATC TGT
viMxA  TGC TGC CTG CTG GCA GAA AAA CTT GAA AAT CAA ATC ATC ACA CAT ATC TGT
       C   C   L   L   A   E   K   L   E   N   Q   I   I   T   H   I   C

MxA    CTG CCC CTG CTG GAG AAT GAG GAG ACT ATC AAG CAG CAC AGA ATA ACA GAG
viMxA  CTG CCC CTG CTG GAG AAT GAG GAG ACT ATC AAG CAG CAC AGA ATA ACA GAG
       L   P   L   L   E   N   E   E   T   I   K   Q   H   R   I   T   E
```

FIG. 10B

```
        GAG CTA CAA AAG TAT GGT GTC GAC ATA CCG GAA GAC GAA AAT GAA AAA ATG
MxA
viMxA   GAG CTA CAA AAG TAT GGT GTC GAC ATA CCG GAA GAC GAA AAT GAA AAA ATG
         E   L   Q   K   Y   G   V   D   I   P   E   D   E   N   E   K   M

MxA     TTC TTC CTG ATA GAT AAA ATT AAT GCC TTT AAT CAG GAC ATC ACT ACT GCT CTC
viMxA   TTC TTC CTG ATA GAT AAA ATT AAT GCC TTT AAT CAG GAC ATC ACT ACT GCT CTC
         F   F   L   I   D   K   I   N   A   F   N   Q   D   I   T   T   A   L

MxA     ATG CAA GGA GAG GAA ACT GTA GGG GAG GAG GAG GAC ATT CGG CTG TTT ACC AGA
viMxA   ATG CAA GGA GAG GAA ACT GTA GGG GAG GAG GAG GAC ATT CGG CTG TTT ACC AGA
         M   Q   G   E   E   T   V   G   E   E   E   D   I   R   L   F   T   R

MxA     CTC CGA CAC CAC GAG TTC CAC AAA TGG AGT AGA AAA ATC CAG AAA TTT GAA AAT CAG TAT
viMxA   CTC CGA CAC CAC GAG TTC CAC AAA TGG AGT AGA AAA ATC CAG AAA TTT GAA AAT CAG TAT
         L   R   H   H   E   F   H   K   W   S   R   K   I   Q   K   F   E   N   Q   Y

1561
MxA     GAA GGC CAT AAA ATT TTG AGT AGA AAA ATC CAG AAA TTT GAA AAT CAG TAT
MxA     GAA                                                               
viMxA   GAA
viMxA    E   G   H   K   I   L

MxA     CGT GGT AGA GAG CTG CCA GGC TTT GTG AAT TAC AGG ACA TTT GAG ACA ATC
MxA
viMxA    R   G   R   E   L   P   G   F   V   N   Y   R   T   F   E   T   I

MxA     GTG AAA CAG CAA ATC AAG GCA CTG GAA GAG CCG GCT GTG GAT ATG CTA CAC
MxA
viMxA    V   K   Q   Q   I   K   A   L   E   E   P   A   V   D   M   L   H

MxA     ACC GTG ACG GAT ATG GTC CGG CTT GCT TTC ACA GAT GTT TCG ATA AAA AAT
MxA
viMxA    T   V   T   D   M   V   R   L   A   F   T   D   V   S   I   K   N
```

FIG. 10C

```
MxA    TTT GAA GAG TTT TTT AAC CTC CAC AGA ACC GCC AAG TCC AAA ATT GAA GAC
MxA     F   E   E   F   F   N   L   H   R   T   A   K   S   K   I   E   D
viMxA   ........................................................... D

MxA    ATT AGA GCA GAA CAA GAG AGA GAA GGT GAG AAG CTG ATC CGC CTC CAC TTC
MxA     I   R   A   E   Q   E   R   E   G   E   K   L   I   R   L   H   F
viMxA   ........................................................... F

MxA    CAG ATG GAA CAG ATT GTC TAC TGC CAG GAC CAG GTA TAC AGG GGT GCA TTG
MxA     Q   M   E   Q   I   V   Y   C   Q   D   Q   V   Y   R   G   A   L
viMxA   ........................................................... L

MxA    CAG AAG GTC AGA GAG AAG GAG CTG GAA GAA GAA AAG AAG AAA TCC TGG
MxA     Q   K   V   R   E   K   E   L   E   E   E   K   K   K   S   W
viMxA   ............................................................

MxA    GAT TTT GGG GCT TTC CAA TCC AGC TCG GCA ACA GAC TCT TCC ATG GAG GAG
MxA     D   F   G   A   F   Q   S   S   S   A   T   D   S   S   M   E   E
viMxA   ............................................................
                                                2050

MxA    ATC TTT CAG CAC CTG ATG GCC TAT CAC CAG GAG GCC AGC AAG CGC ATC TCC
MxA     I   F   Q   H   L   M   A   Y   H   Q   E   A   S   K   R   I   S
viMxA   ......................... Q   GAG GCC AGC AAG CGC ATC TCC
                                  Q    G   A   S   K   R   I   S

MxA    AGC CAC ATC CCT TTG ATC ATC CAG TTC TTC ATG CTC CAG ACG TAC GGC CAG
MxA     S   H   I   P   L   I   I   Q   F   F   M   L   Q   T   Y   G   Q
viMxA  AGC CAC ATC CCT TTG ATC ATC CAG TTC TTC ATG CTC CAG ACG TAC GGC CAG
        A   H   I   P   L   I   I   Q   F   F   M   L   Q   T   Y   G   Q
        Q   P   H   P   F   D   H   P   V   L   H   A   P   D   V   R   P
```

FIG. 10D

```
MxA     CAG CTT CAG AAG GCC ATG CTG CAG GAC AAG GAC ACC TAC AGC
MxA      Q   L   Q   K   A   M   L   Q   D   K   D   T   Y   S
viMxA   CAG CTT CAG AAG GCC ATG CTG CAG GAC AAG GAC ACC TAC AGC
viMxA    A   S   E   G   H   A   A   P   A   G   Q   H   L   Q

MxA     TGG CTC CTG AAG GAG CGG AGC GAC ACC AGC GAC AAG CGG AAG TTC CTG AAG
MxA      W   L   L   K   E   R   S   D   T   S   D   K   R   K   F   L   K
viMxA   TGG CTC CTG AAG GAG CGG AGC GAC ACC AGC GAC AAG CGG AAG TTC CTG AAG
viMxA    L   A   P   E   G   A   E   R   H   Q   R   Q   A   E   V   P   E

MxA     GAG CGG CTT GCA CGG CTG ACG CAG GCT CGG CGC CGG CTT GCC CAG TTC CCC
MxA      E   R   L   A   R   L   T   Q   A   R   R   R   L   A   Q   F   P
viMxA   GAG CGG CTT GCA CGG CTG ACG CAG GCT CGG CGC CGG CTT GCC CAG TTC CCC
viMxA    G   A   C   T   A   D   A   G   S   A   P   A   C   P   V   P
                                                2299

MxA     GGT TAA CCA CAC TCT GTC CAG CCC CGT AGA CGT GCA CGC ACA CTG TCT GCC
MxA      G  (stop)
viMxA   GGT TAA CCA CAC TCT GTC CAG CCC CGT AGA CGT GCA CGC ACA CTG TCT GCC
viMxA    R   L   T   T   L   C   P   P   A   P  (stop)
        2275
```

FIG. 13A

Amino acid sequences in IFNα-induced MxA protein (sequences in exon 17 are highlighted)

MVVSEVDIAKADPAAASHPLLLNGDATVAQKNPGSVAENNLCSQYEEKVRPCIDLIDSL
RALGVEQDLALPAIAVIGDQSSGKSSVLEALSGVALPRGSGIVTRCPLVLKLKKLVNEDK
WRGKVSYQDYEIEISDASEVEKEINKAQNAIAGEGMGISHELITLEISSRDVPDLTLIDLPG
ITRVAVGNQPADIGYKIKTLIKKYIQRQETISLVVVPSNVDIATTEALSMAQEVDPEGDRT
IGILTKPDLVDKGTEDKVVDVVRNLVFHLKKGYMIVKCRGQQEIQDQLSLSEALQREKI
FFENHPYFRDLLEEGKATVPCLAEKLTSELITHICKSLPLLENQIKETHQRITEELQKYGV
DIPEDENEKMFFLIDKINAFNQDITALMQGEETVGEEDIRLFTRLRHEFHKWSTIIENNFQ
EGHKILSRKIQKFENQYRGRELPGFVNYRTFETIVKQQIKALEEPAVDMLHTVTDMVRL
AFTDVSIKNFEEFFNLHRTAKSKIEDIRAEQEREGEKLIRLHFQMEQIVYCQDQVYRGAL
QKVREKELEEEKKKKSWDFGAFQSSSATDSSMEEIFQHLMAYHQEASKRISSHIPLIIQFF
MLQTYGQQLQKAMLQLLQDKDTYSWLLKERSDTSDKRKFLKERLARLTQARRRLAQF
PG (SEQ ID NO://)

FIG. 13B

Amino acid sequences in alphaherpesvirus-induced MxA variant protein (sequences in exon 17 are highlighted)

MVVSEVDIAKADPAAASHPLLLNGDATVAQKNPGSVAENNLCSQYEEKVRPCIDLIDSL
RALGVEQDLALPAIAVIGDQSSGKSSVLEALSGVALPRGSGIVTRCPLVLKLKKLVNEDK
WRGKVSYQDYEIEISDASEVEKEINKAQNAIAGEGMGISHELITLEISSRDVPDLTLIDLPG
ITRVAVGNQPADIGYKIKTLIKKYIQRQETISLVVVPSNVDIATTEALSMAQEVDPEGDRT
IGILTKPDLVDKGTEDKVVDVVRNLVFHLKKGYMIVKCRGQQEIQDQLSLSEALQREKI
FFENHPYFRDLLEEGKATVPCLAEKLTSELITHICKSLPLLENQIKETHQRITEELQKYGV
DIPEDENEKMFFLIDKINAFNQDITALMQGEETVGEEDIRLFTRLRHEFHKWSTIIENNFQ
EGGQQAHLQPHPFDHPVLHAPDVRPAASEGHAAAPAGQGHLQLAPEGAERHQRQAEV
PEGAACTADAGSAPACPVPRLTTLCPAP. (SEQ ID NO://)

FIG. 14
 

FIG. 16

```
 841 agagtggctg tggcaatca gcctgctgac attgggtata agatcaagac actcatcaag
 901 aagtacatcc agaggcagga gacaatcagc ctggtggtgg tccccagtaa tgtggacatt
 961 gccaccacag aggctctcag catggcccag gaggtggacc ccgagggaga cagga^m4 ccatc
1021 ggaatcttga cgaagcctga tctggtggac aaaggaactg aagacaaggt tgtggacgtg
1081 gtgcggaacc tcgtgttcca cctgaagaag ggttacatga ttgtcaagtg ccggggccag
1141 caggagatcc aggaccagct gagcctgtcc gaagccctgc a^m6 gagagagaa gatctttctt
1201 gagaaccacc catatttcag ggatctgctg gaggaaggaa aggccacggt tccctgcctg
1261 gcagaaaaac ttac^m5 cagcga gctcatcaca catatctgta aatctctgcc cctgttagaa
          Ex14
1321 aatcaaatca aggagactca ccagagaata acagaggagc tacaaaagta tggtgtcgac
1381 ataccggaag acgaaaatga aaaaat^m2 gttc ttcctgatag ataaaattaa tgcctttaat
1441 caggacatca ctgctctcat gcaaggagag gaaactgtag gggaggaaga cattcggctg
1501 tttaccagac tc^m3 cgacacga gttccacaaa tggagtacaa taattgaaaa caatttcaa
1561 gaaggccata aaatttttgag tagaaaaatc cagaaatttg aaaatcagta tcgtggtaga
1621 gagctgccag gctttgtgaa ttacaggaca tttgagacaa tcgtgaaaca gcaaatcaag
1681 gcactggaag agccggctgt ggatatgcta cacaccgtga cggatatggt ccggcttgct
1741 t^m1 tcacagatg tttcgataaa aaattttgaa gagtttttta acctccacag aaccgccaag
1801 tccaaaattg aagacattag agcagaacaa gagagagaag gtgagaagct gatccgcctc
1861 cacttccaga tgtctactgc caggaccagg tatacagggg tatacaggg tgcattgcag
```

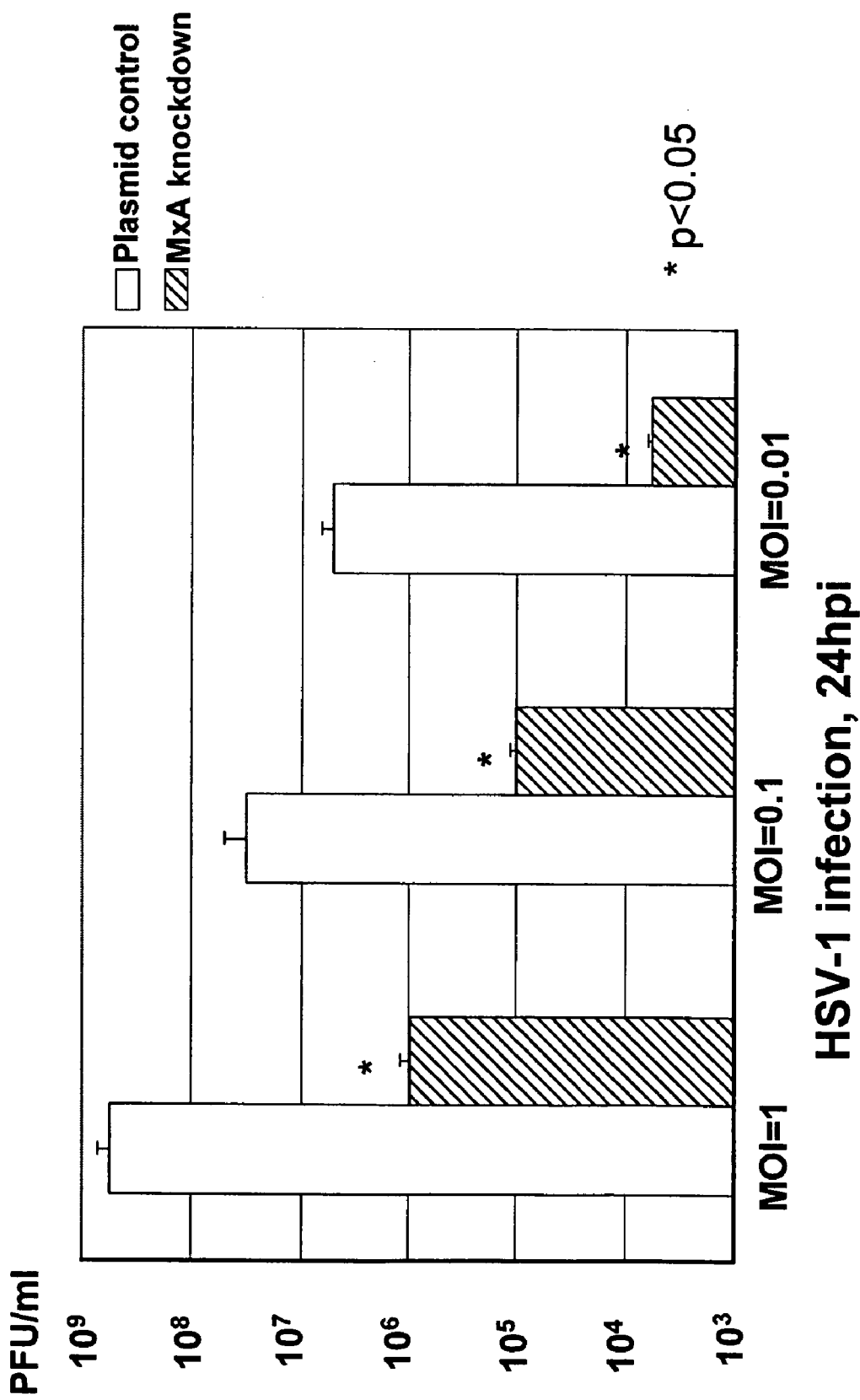

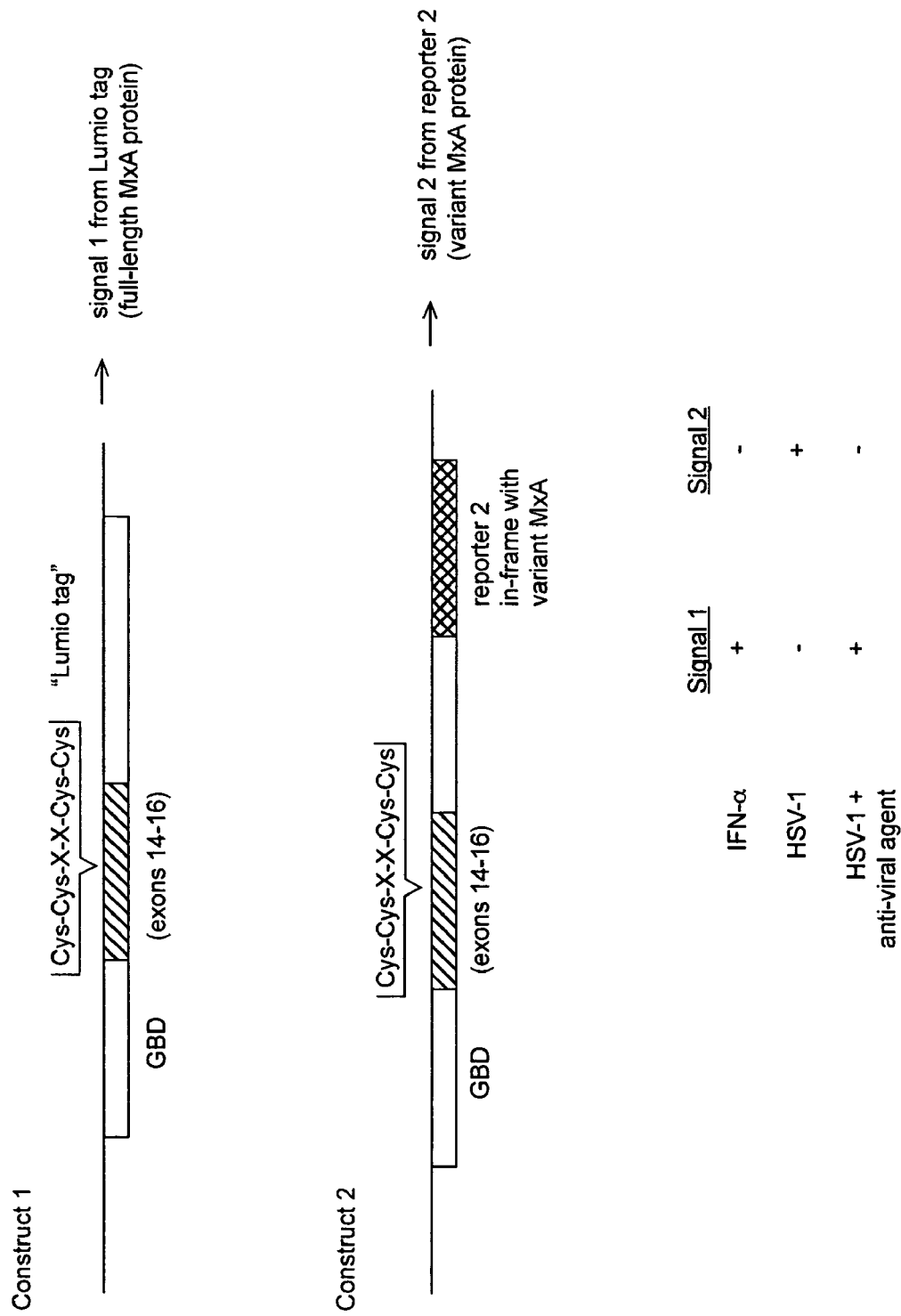

MXA AS AN ANTIVIRAL DRUG AND AS A TARGET FOR IDENTIFICATION OF ANTIVIRAL DRUGS FOR DNA VIRUS INFECTIONS

CROSS-REFERENCE TO RELATED APPLICATIONS

This application claims the benefit of U.S. Provisional Application No. 60/784,277, filed Mar. 20, 2006, which application is incorporated herein by reference.

GOVERNMENT RIGHTS

This invention was made with government support under federal grant no. AI020459 awarded by National Institutes of Health. The United States Government may have certain rights in this invention.

BACKGROUND

MxA (sometimes referred to as Mx1) is a cytoplasmic protein having a GTP-binding domain and GTPase activity. MxA has been implicated in mediating antiviral activity against several RNA viruses. The nucleotide and amino acid sequences of MxA are available at, for example, GenBank Acc. No. BC032602.

SUMMARY OF THE INVENTION

The invention features methods and compositions for use in a screening assay to identify agents having antiviral activity against a DNA virus by assessing the effect of a candidate agent upon alternative splicing of MxA, by assessing the effect of the candidate agent on the levels of MxA and/or variant MxA transcript, or by assessing the effect of a candidate agent on production of a variant form of MxA protein. The invention also provides methods for enhancing resistance of cells to infection by a DNA virus by providing for elevated MxA and/or by providing for reduced production of variant MxA protein.

BRIEF DESCRIPTION OF THE FIGURES

This application contains drawings executed in color. Copies of this patent or patent application publication with color drawings will be provided by the U.S. Patent and Trademark Office upon request and payment of the necessary fee.

Titles for each of the Figures are provided. For a detailed description of each of the Figures, see Examples section below.

FIGS. 9A and 9B. Full length MxA coding sequence (SEQ ID NO:6). Exon 14-16 sequences are boxed. FIG. 9C. Variant MxA coding sequence (SEQ ID NO:7). The start and stop codons are underlined and in bold in FIGS. 9A and 9C.

FIGS. 10A-D. Sequence analysis comparing amino acid sequences of MxA and the variant MxA protein induced by HSV (vMxA). FIGS. 10A-D provide an MxA-encoding nucleotide sequence (SEQ ID NO:16); a vMxA-encoding nucleotide sequence (SEQ ID NO:17); an MxA amino acid sequence (SEQ ID NO:18); and a vMxA amino acid sequence (SEQ ID NO:19). The amino acid sequence of the polypeptide fragment present in MxA (exons 14-16) but not in the variant MxA protein is indicated by highlighting. The nucleotides and amino acids demarcating the central interaction domain of MxA are indicated in bold and double underlining. The codons that are generated by the splice junction and that give rise to the frameshift in the coding sequence relative to the unspliced parent transcript (which results in the C-terminal amino acid sequence of variant MxA) are denoted with alternating underlining and bold.

FIG. 13A. Amino acid sequence of full-length MxA protein (SEQ ID NO:5).

FIG. 13B. Amino acid sequence of variant MxA protein (SEQ ID NO:4).

FIG. 14. Expression of full-length MxA mRNA and variant MxA mRNA by transfection of melanoma cells.

FIG. 16. Target sequences for siRNA knockdown. Exemplary target sequences are underlined and in bold. Nucleotides 841-1920 of SEQ ID NQ:6 are shown, this nucleotide sequence is designated SEQ ID NO:20.

FIG. 18. Inhibition of MxA expression by siRNA reduced the yield of infectious HSV-1.

FIG. 20. An exemplary drug screening assay for identifying agents that reduce levels of variant MxA protein.

Figure 1:
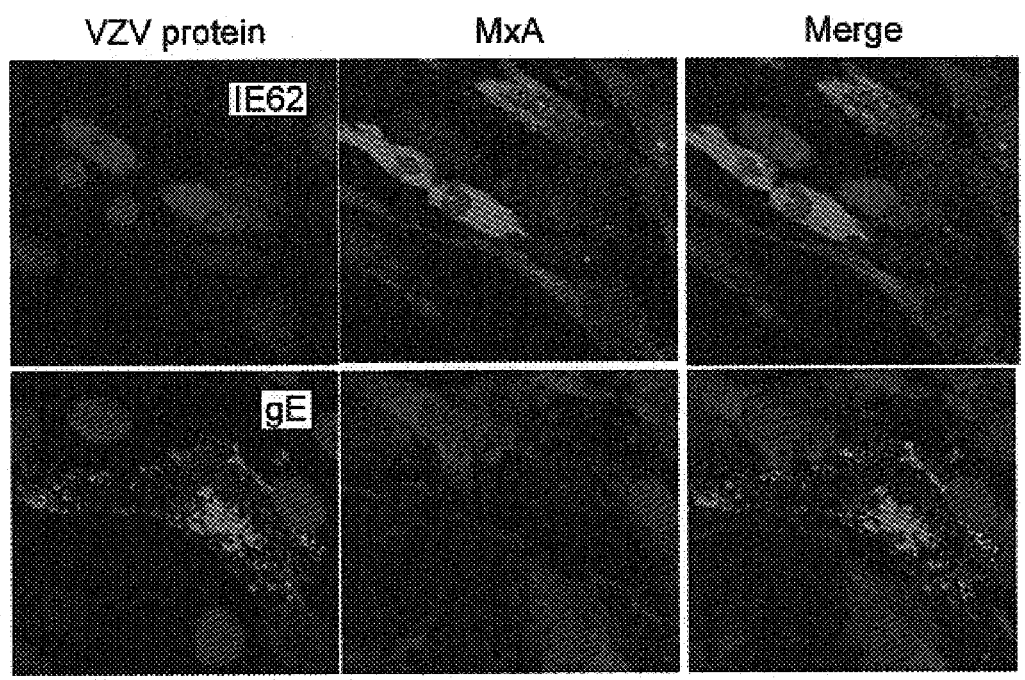
FIG. 1. VZV does not infect MxA expressing cells in IFN-α treated cell monolayer.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DETAILED DESCRIPTION OF THE INVENTION

The inventors have observed that MxA inhibits DNA virus infection (e.g., herpesviruses), and further that DNA viruses have developed a means to evade MxA activity by directing the host cell transcription/translation machinery to translate a splice variant of MxA mRNA, referred to herein as variant MxA mRNA ("vMxA mRNA"), generating a variant MxA protein that has a functional deletion of a sequence containing the active antiviral domain and has a C-terminal amino acid sequence that differs from the C-terminal sequence of the full-length MxA protein.

Both full-length MxA and variant MxA transcripts are present in cells not infected with a DNA virus. However, infection of a cell with a DNA virus results in a shift from translation of the MxA transcript to translation of the vMxA transcript, such that MxA protein is at very low or undetectable levels in the infected cell, and such that variant MxA (vMxA) protein production in the cell is markedly increased. Therefore, DNA virus-infected cells have markedly increased levels of vMxA protein and low or undetectable levels of MxA protein.

MxA and vMxA proteins share a common amino acid sequence, from the N-terminus of the proteins up to an including amino acid residues encoded by exon 13, e.g., from the N-terminus up to an including the $Glu^{424}$. However, due to deletion of exons 14-16 from the vMxA transcript, and a frameshift in exon 17, the amino acid sequence C-terminal to the exon 13-encoded amino acid sequence differs between MxA and vMxA. These differences can be exploited to differentially detect MxA and vMxA. For example, the M143 antibody, which recognizes an epitope in the GTP-binding domain, binds both MxA and vMxA proteins, while the 2C12 antibody, which recognizes an epitope within amino acids 432-471 of the MxA protein, binds MxA, but not vMxA. In the context of detection of MxA and vMxA proteins, reference to the "N-terminal domain" or "N-terminal region" of MxA and vMxA proteins refers to an amino acid sequence common to MxA and vMxA, e.g., the amino acid sequence N-terminal to and including $Glu^{424}$ or a portion thereof which is distinct from the C-terminal region. Reference to the "C-terminal domain" or "C-terminal region" of MxA and vMxA proteins refers to a portion of the MxA and vMxA proteins C-terminal to $Glu^{424}$ or a portion thereof that is distinct from the N-terminal region. The "C-terminal region" of MxA includes amino acids encoded by exons 14-17; and the "C-terminal region" of vMxA includes amino acids encoded by exon 17, e.g., the boxed portion of the amino acid sequence depicted in FIG. 13B.

The variant MxA protein is referred to herein as "variant MxA protein" and is abbreviated "vMxA" or "vMxA" protein. The vMxA protein enters the nucleus and localizes at sites of viral DNA replication. Interventions that prevent the production of the MxA splice variant and/or enhance full-length MxA and/or reduce production of vMxA protein and/or disrupt translocation of vMxA to the nucleus can serve as antiviral agents for DNA viruses such as herpesviruses.

Definitions

"vMxA" ("variant MxA mRNA"), that encodes a variant of MxA protein having at least a functional deletion in a sequence containing the antiviral domain of MxA, which domain normally has functions in recognition of viral nucleocapsids and facilitating GTPase activity. "vMxA" may also be referred to as "viMxA" in view of the "viral induction" of increased levels of vMxA protein.

A "functional deletion" as used in the context of a functional deletion of an antiviral domain(s) of MxA is meant to indicate that the vMxA has reduced antiviral activity relative to MxA encoded by the parent transcript in that the vMxA polypeptide encoded by the vMxA splice product lacks at least a portion of a functional domain which corresponds to an antiviral activity in MxA.

An "antiviral domain of MxA" refers a nucleic acid sequence encoding a portion of MxA polypeptide, or the corresponding amino acid sequence of the MxA polypeptide fragment, which facilitates GTPase activity and/or viral nucleocapsid binding by MxA. The structure of full-length MxA, which is the "parent" of the vMxA proteins described herein, is well known. The N-terminal half of MxA (amino acids 1-363 in human MxA) contains the sequence elements necessary for GTP binding. The central interactive domain of MxA (amino acids 372-540 in human MxA, which amino acids are encoded by the nucleic acid sequence located in exons 13-16) has the function in the recognition of viral nucleocapsid structure and stimulation of MxA GTPase activity. Binding of 2C12 mAb which recognizes this central region reduces MxA GTP hydrolysis and abolishes its antiviral activity against RNA viruses (Flohr et al., FEBS Letters, 463:24-28, 1999).

"DNA virus" as used herein refers to a virus having a DNA genome. Exemplary DNA viruses include herpesvirus (e.g., HSV1, HSV2, CMV, VZV, EBV, HHV-6, HHV-7, HHV-8 pseudorabies, and the like); erythroviruses (also referred to as parvoviruses) (e.g., B19, V9, A6); papoviruses; adenoviruses; hepadnaviruses (e.g., HBV); and poxviruses. In some embodiments, the DNA virus is other than HBV. Herpesviruses are of particular interest.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (A or T (U)); S=C or G; W=A or T (U); M=A or C; K=G or T (U); V=A, C or G; and N=any nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides. The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, e.g., constituting at least about 0.5%, or at least about 5% by weight of the total protein in a given sample. For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

"Purified" as used herein means that the recited material comprises at least about 75%, at least about 80%, at least about 90%, at least about 95%, or at least about 99% by weight of the total material. As used herein, the term "substantially pure" refers to a compound that is removed from its natural environment and is at least 60% free, at least 75% free, at least 90% free, at least 95% free, or at least 99% free from other components with which it is naturally associated.

A polynucleotide "derived from" or "specific for" a designated sequence, such as a target sequence of a target nucleic acid, refers to a polynucleotide sequence which comprises a contiguous sequence of approximately at least about 6 nucleotides, at least about 8 nucleotides, at least about 10-12 nucleotides, or at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientation relative to the original polynucleotide.

"Contiguous" as used herein, such as in the context of two contiguous nucleic acids, means that two sequences are connected without intervening nucleotides.

"Homology" refers to the percent similarity between two polynucleotide or two polypeptide moieties. Two DNA, or two polypeptide sequences are "substantially homologous" to each other when the sequences exhibit at least about 50%, at least about 75% at least about 80%, at least about 85%, at least about 90%, at least about 95% or at least about 98% sequence similarity over a defined length of the molecules. As used herein, substantially homologous also refers to sequences showing complete Identity to the specified DNA or polypeptide sequence.

Sequence "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as Lasergene from DNASTAR, Inc., and ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology or percent identity is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet on a website sponsored by the National Center for Biotechnology Information (NCBI) and the National Library of Medicine (see the world wide website at ncbi.nlm.gov/cgi-bin/BLAST).

Alternatively, homology and identity can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for or facilitate the transcription and translation of a coding sequence in a host cell.

As used herein, the term "target nucleic acid region" or "target nucleic acid" or "target polypeptide region" or "target polypeptide" or "target molecules" refers to a nucleic acid molecule with a "target sequence" to be detected (e.g., by amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" or "target amino acid sequence" refers to the particular nucleotide sequence of a target nucleic acid or a particular amino acid sequence of a target polypeptide to be detected (e.g., through amplification). Where the target is a polypeptide, the target sequence can be an epitope that provides to specific binding of an antibody, e.g., that specifically binds vMxA relative to MxA, or an antibody that specifically binds MxA relative to vMxA.

Where the target is nucleic acid, the target sequence may include a probe-hybridizing region contained within the target molecule with which a probe will form a stable hybrid under desired conditions and/or may include the complexing sequences to which the oligonucleotide primers complex and be extended using the target sequence as a template. Where the target nucleic acid is single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands.

The invention also contemplates target regions having the full-length of the sequences provided herein, as well as fragments or subsequences of such target regions, and complementary sequences thereof. The terms "fragment" and "subsequence" are used interchangeably in this context. Moreover, where nucleic acid sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are in some embodiments in the range of between 8 to 100 nucleotides in length, such as 10 to 75, 15 to 60, 15 to 40, 18 to 30, 20 to 40, 21 to 50, 22 to 45, 25 to 40 nucleotides, and so on, e.g., in the range of between 18-40, 20-35, 21-30 nucleotides long, and any length between the stated ranges. Primers can be in the range of between 10-50 nucleotides long, such as 15-45, 18-40, 20-30, 21-25 nucleotides long, and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Primers will in some embodiments be single-stranded for maximum efficiency in amplification, but may alternatively be double-stranded. If double-stranded, the primer can be first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are usually are in the range of between 8 to 100 nucleotides in length, such as 8 to 75, 10 to 74, 12 to 72, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. The typical probe is in the range of between 10-50 nucleotides long, such as 15-45, 18-40, 20-30, 21-28, 22-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TaqMan™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO4, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50. ° C. or about 55° C. to about 60° C.; or, a salt concentration of about 0.15 M NaCl at 72° C. for about 15 minutes; or, a salt concentration of about 0.2×SSC at a temperature of at least about 50° C. or about 55. ° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37. ° C. (for 14-base oligos), 48. ° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Variant MxA (vMxA) Protein

Figure 11:
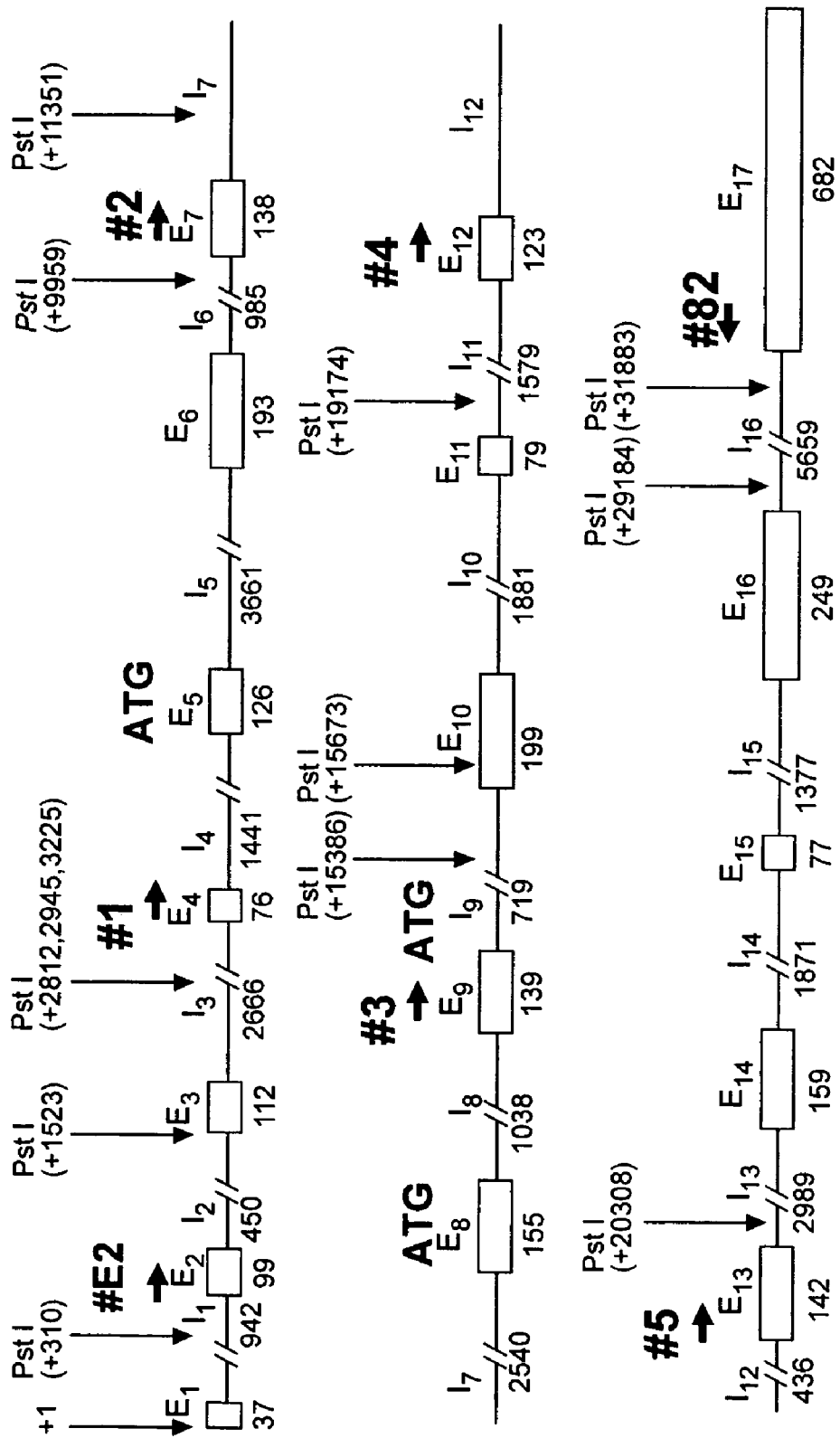
FIG. 11. Schematic showing MxA gene structure, RT-PCR primer binding sites and splicing of a MxA splice variant induced by HSV (modified from FIG. 1 of Tazi-Ahnini et al. (2000) Human Genetics 106:639-645).

As illustrated in detail in the Examples, infection of a cell with a DNA virus results in a shift from translation of the MxA transcript to translation of the vMxA transcript, such that MxA protein is at very low or undetectable levels in the infected cell, and such that variant MxA (vMxA) protein production in the cell is markedly increased. Therefore, DNA virus-infected cells have markedly increased levels of vMxA protein and low or undetectable levels of MxA protein. An exemplary vMxA splice variant is illustrated in FIG. 11. This vMxA, which is present in uninfected cells as well as in HSV-infected cells, is produced by splicing of exon 13 to exon 17, with deletion of the intervening sequences, including those encoding exons 14-16. The region deleted in vMxA mRNA relative to MxA mRNA corresponds to sequences encoding an active antiviral domain of MxA, which is known to have activity in viral nucleocapsid recognition and in facilitating GTPase activity. In addition to deleting exons 14-16, the vMxA splice variant also includes a frameshift, such that the amino acid sequence encoded by exon 17 in the vMxA protein differs from the amino acid sequence encoded by exon 17 in the MxA protein. As a consequence, the amino acid sequence C-terminal to the exon 13-encoded amino acid sequence differs dramatically between the vMxA and the MxA proteins. This difference is illustrated in FIGS. 10A-D.

Production of vMxA protein is directed by a DNA virus, following infection of a mammalian cell by the DNA virus, e.g., herpesviridae. As illustrated in the Examples, vMxA protein translocates to the nucleus in DNA virus infected cells. This translocation event serves as a marker for DNA virus infection and for DNA virus replication.

vMxA Nucleic Acids

The present invention provides vMxA nucleic acids, e.g., isolated vMxA nucleic acids, where "vMxA nucleic acids" include: 1) a nucleic acid comprising a nucleotide sequence encoding all or a portion of a vMxA polypeptide, where vMxA polypeptides are described in more detail below; 2) nucleic acid primers and nucleic acid probes that are suitable for detecting MxA RNA or vMxA RNA; and 3) an interfering nucleic acid, e.g., a nucleic acid that reduces production of a vMxA polypeptide. Also provided are vectors (e.g., recombinant constructs) comprising a subject vMxA nucleic acid, as well as host cells comprising a subject vMxA nucleic acid or recombinant vector.

The present disclosure provides isolated polynucleotides encoding a vMxA variant protein, wherein the vMxA polypeptide lacks at least a portion of an antiviral domain as defined above, and has a different amino acid sequence from MxA in the region C-terminal to the exon 13-encoded amino acid sequence. In one embodiment, the vMxA is a splice variant product which comprises a splice junction comprising the 3' end of exon 13 and the 5' end of exon 17, where the 3' end of exon 13 and the 5' end of exon 17 are contiguous, as depicted in FIGS. 10A-D. (see, e.g., FIG. 9C). An exemplary nucleotide sequence of a vMxA nucleic acid comprising the contiguous sequence of MxA exon 13 and exon 17 is provided in FIG. 9C. The coding sequence that appears in MxA, but not in vMxA is indicated in FIGS. 9A and 9B (the sequence in the boxed portion). For example, the nucleotide sequence TTTCAAGAAGGAGGCCAGCAAG (SEQ ID NO:1; 22 nts)

comprises the splice junction of MxA exon 13 and exon 17, where the "G" at residue 10 is from the 3' end of MxA exon 13, and the "G" at residue 11 is from the first nucleotide of MxA exon 17.

The disclosure contemplates polynucleotides comprising a sequence encoding a full-length vMxA polypeptide or a fragment thereof that comprises a sequence unique relative to MxA. In one embodiment, a unique nucleotide sequence of vMxA relative to MxA is the nucleotide sequence, AAG-GAGG, which bridges the splice junction of MxA exons 13 and 17. The disclosure also contemplates nucleic acids encoding a full-length vMxA or a fragment thereof that comprises an amino acid sequence unique to vMxA. For example, as illustrated in FIGS. 10A-D, the vMxA induced by HSV contains the amino acid sequence NNFQEGGQQA (SEQ ID NO:2) at the splice junction, where the "E" is encoded by the last codon of exon 13, and where the first "G" is encoded by the last nucleotide (G) of exon 13 and the first two nucleotides (GA) of exon 17. In contrast, the sequence of MxA is NNFQEGHKIL (SEQ ID NO:3), where the "E" is encoded by the GAA codon near the 3' end of exon 13, and the "G" is encoded by the last nucleotide (G) of exon 13 and the first two nucleotides (GC) of exon 14. The nucleotides and amino acids demarcating the central region ("CID" or central interaction domain") of MxA, which plays a role in recognition of viral nucleocapsid structure and stimulation of MxA GTPase activity, are indicated in bold and double underlining.

In some embodiments, a subject vMxA nucleic acid comprises a nucleotide sequence encoding a vMxA polypeptide having at least about 75%, at least about 80%, at least about 85%, at least about 90%, at least about 95%, at least about 97%, at least about 98%, at least about 99%, or 100% amino acid sequence identity to the vMxA amino acid sequence set forth in FIG. 13B (SEQ ID NO:4).

In some embodiments, a subject vMxA nucleic acid comprises a nucleotide sequence encoding a vMxA polypeptide having at least about 75%, at least about 80%, at least about 85%, at least about 90%, at least about 95%, at least about 97%, at least about 98%, at least about 99%, or 100% amino acid sequence identity to a sequence of at least about 20, at least about 25, at least about 30, at least about 50, at least about 75, at least about 85, at least about 90, at least about 100, at least about 125, at least about 150, at least about 175, at least about 200, at least about 225, at least about 250, at least about 275, at least about 300, at least about 325, at least about 350, at least about 375, at least about 400, at least about 425, at least about 450, at least about 475, or at least about 500 contiguous amino acids of the vMxA amino acid sequence set forth in FIG. 13B (SEQ ID NO:4).

In some embodiments, a subject vMxA nucleic acid comprises a nucleotide sequence encoding a vMxA polypeptide having at least about 75%, at least about 80%, at least about 85%, at least about 90%, at least about 95%, at least about 97%, at least about 98%, at least about 99%, or 100% amino acid sequence identity to the amino acid sequence of amino acids 425 to 508 of the vMxA amino acid sequence set forth in FIG. 13B (SEQ ID NO:4). The amino acid sequence of amino acids 425 to 508 of the vMxA as set forth in FIG. 13B is not present in the MxA protein (e.g., full-length MxA protein). In some embodiments, a subject vMxA nucleic acid comprises a nucleotide sequence encoding from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 70 to about 75, from about 75 to about 80, or from about 80 to about 84 contiguous amino acids of the amino acid sequence of amino acids 425 to 508 of the vMxA amino acid sequence set forth in FIG. 13B (SEQ ID NO:4).

In some embodiments, a subject vMxA nucleic acid comprises a nucleotide sequence having at least about 75%, at least about 80%, at least about 85%, at least about 90%, at least about 95%, at least about 97%, at least about 98%, at least about 99%, or 100% nucleotide sequence identity to the nucleotide sequence set forth in FIG. 9C (SEQ ID NO:7). In some embodiments, a subject vMxA nucleic acid comprises a nucleotide sequence having at least about 75%, at least about 80%, at least about 85%, at least about 90%, at least about 95%, at least about 97%, at least about 98%, at least about 99%, or 100% nucleotide sequence identity to the nucleotide sequence set forth in nucleotides 292-1815 of the nucleotide sequence set forth in FIG. 9C (SEQ ID NO:7).

In other embodiments, a subject vMxA nucleic acid comprises a nucleotide sequence having at least about 75%, at least about 80%, at least about 85%, at least about 90%, at least about 95%, at least about 97%, at least about 98%, at least about 99%, or 100% nucleotide sequence identity to the nucleotide sequence set forth in nucleotides 1564 to 1815 of the nucleotide sequence set forth in FIG. 9C (SEQ ID NO:7).

In some embodiments, a subject vMxA nucleic acid comprises all or a portion of the nucleotide sequence set forth in FIG. 9C (SEQ ID NO:7). In some embodiments, a subject vMxA nucleic acid comprises a nucleotide sequence including at least nucleotides 1564 to 1815 of the sequence set forth in FIG. 9C, e.g., encoding amino acids 425 to 508 of vMxA.

In some embodiments, a subject vMxA nucleic acid comprises a nucleotide sequence encoding a fusion protein, where the fusion protein comprises a vMxA protein and a fusion partner, e.g., a polypeptide other than vMxA. In some embodiments, the fusion partner is attached to the N-terminus of the vMxA protein, e.g., $NH_2$-fusion partner-vMxA-COOH. In other embodiments, the fusion partner is attached to the C-terminus of the vMxA protein, e.g., $NH_2$-vMxA-fusion partner-COOH. In other embodiments, the fusion partner is internal to the vMxA protein, e.g., $NH_2$— $(vMxA)_1$-FP-$(vMxA-COOH)_2$, where FP is a fusion partner, and $vMxA_1$ and $vMxA_2$ are N-terminal and C-terminal domains, respectively, of vMxA, Suitable fusion partners include, but are not limited to, immunological tags such as epitope tags, including, but not limited to, hemagglutinin, FLAG, myc, and the like; proteins that provide for a detectable signal, including, but not limited to, fluorescent proteins, enzymes (e.g., β-galactosidase, luciferase, horse radish peroxidase, alkaline phosphatase, etc.), and the like; polypeptides that facilitate purification or isolation of the fusion protein, e.g., metal ion binding polypeptides such as 6His tags, glutathione-5-transferase, and the like; polypeptides that provide for subcellular localization; and polypeptides that provide for secretion from a cell. Fusion partners that provide for a detectable signal are also referred to as "reporters."

Suitable reporter fusion partners, especially at a C-terminus or N-terminus of the vMxA, particularly the C-terminus, include, but are not limited to, luciferase (e.g., firefly luciferase and derivatives thereof; *Renilla* luciferase and derivatives thereof); β-galactosidase; chloramphenicol acetyl transferase; glutathione S transferase; a green fluorescent protein-(GFP), including, but not limited to, a GFP derived from *Aequoria victoria* or a derivative thereof, a number of which are commercially available; a GFP from a species such as *Renilla reniformis, Renilla mulleri,* or *Ptilosarcus guernyi,* as described in, e.g., WO 99/49019 and Peelle et al. (2001) *J. Protein Chem.* 20:507-519; a truncated GFP as described in Li et al. (1997) *J. Biol. Chem.* 272:28545-28549; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; a red fluorescent protein; a yellow fluorescent protein; a Lumio™ tag (e.g., a peptide of the sequence Cys-Cys-Xaa-Xaa-Cys-Cys, where Xaa is any amino acid other than cysteine, e.g., where Xaa-Xaa is Pro-Gly, which peptide is specifically bound by a fluorescein derivative having two As(III) substituents, e.g., 4',5'-bis(1,3,2-dithioarsolan-2-yl)fluorescein; see, e.g., Griffin et al. (1998) *Science* 281:269; Griffin et al. (2000) *Methods Enzymol.* 327:565; and Adams et al. (2002) *J. Am. Chem. Soc.* 124:6063); and the like.

In some embodiments, a subject vMxA nucleic acid comprises a nucleotide sequence encoding a fusion protein, where the fusion protein comprises a vMxA protein comprising an amino acid sequence of amino acids 425 to 508 of the amino acid sequence set forth in FIG. 13B (SEQ ID NO:4) and a fusion partner. In some embodiments, a subject vMxA nucleic acid comprises a nucleotide sequence encoding a fusion protein, where the fusion protein comprises a vMxA protein comprising an amino acid sequence of amino acids 425 to 508 of the amino acid sequence set forth in FIG. 13B (SEQ ID NO:4), and where the fusion partner provides for a detectable signal.

All or portions of the nucleic acids described herein can be provided in constructs, which constructs can be introduced into suitable host cells (e.g., mammalian cells, e.g., human cells or cell lines) for use in detection of MxA and/or vMxA transcripts. Such constructs can generally contain at least a donor splice site and an acceptor splice site of exons that are joined by a splicing event that results in production of vMxA. For example, MxA/vMxA splicing events can be detected using a reporter construct which provides for either an increase or decrease in a detectable signal upon a splicing event that joins a donor splice site of a MxA exon 13 to an acceptor splice site of an MxA exon 17. The MxA nucleic acids in the reporter construct can be operably linked to a nucleic acid heterologous to the MxA nucleic acid, which heterologous nucleic acid can provide for a detectable signal (e.g., can encode a reporter protein). In some embodiments, such reporter constructs can also find use in monitoring nuclear translocation of vMxA protein, e.g., by virtue of a detectable fluorescent reporter polypeptide operably linked and downstream of the acceptor splice site to provide, e.g., a vMxA fusion protein.

The disclosure also contemplates polynucleotides obtained from the biological materials described herein or other biological sources (particularly human sources) by hybridization under stringent conditions (particularly conditions of high stringency); polynucleotides having endogenous or exogenous (i.e. heterologous) flanking sequences. Other nucleic acid compositions contemplated by and within the scope of the present invention will be readily apparent to one of ordinary skill in the art when provided with the disclosure here.

Nucleic acid compositions described herein of particular interest are at least 20 nts in length, at least about 25 nts in length, at least about 30 nts in length, at least about 35 nts in length, at least about 40 nts in length, at least about 50 nts in length, at least about 100 nts, at least about 200 nts in length, at least about 300 nts in length, at least about 500 nts in length, at least about 800 nts in length, and up to 1 kb or more. These polynucleotides (or polynucleotide fragments) have uses that include, but are not limited to, probes and primers, as starting materials for probes and primers, for producing of a polypeptide having the amino acid sequence encoded by the 13-17 exon splice junction, and for production of a vMxA protein (e.g., the C-terminal portion of the vMxA protein encoded by exon 17).

MxA homologs are found in many species including, for example, human, mouse, rat, swine, and fish. The human MxA and mouse Mx2 proteins are closely related, showing 77% sequence identity (Aebi et. al., Molecular and Cellular Biology 9:5062, 1989, incorporated herein by reference for its disclosure of MxA and MxA homolog sequences. Since the observations made in the Examples below can be extended to a general mechanism of evasion of a host antiviral response by modification of a host MxA transcript to generate a functional deletion of an antiviral domain, splice variants of vMxA homologs of the human vMxA splice variant described herein are reasonably expected to be found in mammalian cells other than human cells. Thus the present disclosure contemplates nucleic acids that are variants (including degenerate variants) of a sequence provided herein. In general, a variants of a polynucleotide provided herein have a fragment of sequence identity that is greater than at least about 65%, greater than at least about 70%, greater than at least about 75%, greater than at least about 80%, greater than at least about 85%, or greater than at least about 90%, 95%, 96%, 97%, 98%, 99% or more (i.e. 100%) as compared to an identically sized fragment of a provided sequence. as determined by the Smith-Waterman homology search algorithm as implemented in MPSRCH program (Oxford Molecular). For the purposes of this invention, a preferred method of calculating percent identity is the Smith-Waterman algorithm. Global DNA sequence identity should be greater than 65% as determined by the Smith-Waterman homology search algorithm as implemented in MPSRCH program (Oxford Molecular) using an gap search with the following search parameters: gap open penalty, 12; and gap extension penalty, 1. By using probes, particularly labeled probes of DNA sequences, one can isolate homologs, e.g., from non-human mammals, including other primate species; rodents, such as rats and mice; canines, felines, bovines, ovines, equines, and the like.

In one embodiment, hybridization is performed using a fragment of at least 15 contiguous nucleotides (nt) of at least one of the polynucleotide sequences provided herein. That is, when at least 15 contiguous nt of one of the disclosed polynucleotide sequences is used as a probe, the probe will preferentially hybridize with a nucleic acid comprising the complementary sequence, allowing the identification and retrieval of the nucleic acids that uniquely hybridize to the selected probe. Probes from more than one polynucleotide sequence provided herein can hybridize with the same nucleic acid if the cDNA from which they were derived corresponds to one mRNA.

Polynucleotides of the present disclosure also include those having a sequence of naturally occurring variants of the nucleotide sequences (e.g., degenerate variants (e.g., sequences that encode the same polypeptides but, due to the degenerate nature of the genetic code, different in nucleotide sequence), allelic variants, etc.). Variants of the polynucleotides contemplated by the invention can be identified by hybridization of putative variants with nucleotide sequences disclosed herein, preferably by hybridization under stringent conditions. For example, by using appropriate wash conditions, variants of the polynucleotides described herein can be identified where the allelic variant exhibits at most about 25-30% base pair (nts) mismatches relative to the selected polynucleotide probe. In general, allelic variants contain 15-25% bp mismatches, and can contain as little as even 5-15%, or 2-5%, or 1-2% bp mismatches, as well as a single bp mismatch.

The nucleic acid compositions of the subject invention can encode all or a part of the naturally-occurring polypeptides. Double or single stranded fragments can be obtained from the DNA sequence by chemically synthesizing oligonucleotides in accordance with conventional methods, by restriction enzyme digestion, by PCR amplification, etc.

The polynucleotides of interest can be isolated and obtained in substantial purity, generally as other than an intact chromosome. In some embodiments, the polynucleotides, either as DNA or RNA, will be obtained substantially free of other naturally-occurring nucleic acid sequences that they are usually associated with, e.g., the polynucleotide is at least about 50%, or at least about 90% pure and are in some embodiments "recombinant", and can be flanked by one or more nucleotides with which it is not normally associated on a naturally occurring chromosome.

The polynucleotides described herein can be provided as a linear molecule or within a circular molecule, and can be provided within autonomously replicating molecules (vectors) or within molecules without replication sequences. Expression of the polynucleotides can be regulated by their own or by other regulatory sequences known in the art. The polynucleotides can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Primers and Probes

As described above, the disclosure provides methods of detecting a vMxA-encoding nucleic acid so as to distinguish between a MxA-encoding and a vMxA-encoding sequence. Primers and probes for use in these assays are usually designed so as to detect a sequence of the splice junction generated by a splicing event that generates a vMxA transcript, which generally provides for a functional deletion of an antiviral domain normally encoded in the parent MxA transcript. For example, in the exemplary vMxA transcript, a unique sequence is generated as a result of splicing of exons 13 and 17 of a MxA transcript to produce a vMxA. For example, the sequence TTTCAAGAAGGAGGCCA (SEQ ID NO:8), which comprises the splice junction of MxA exon 13 and exon 17 (where the "G" at residue 10 is from the 3' end of MxA exon 13, the "G" at residue 11 is from the 5' end of MxA exon 17) is a target sequence of particular interest for detection of vMxA transcripts. Primers and probes that provide for detection of the splice junction between MxA exons 13 and 17 find use in detection of nucleic acid encoding the vMxA splice variant. For example, a primer or probe can be designed so as to detect the sequence GAAGGAGG, which bridges the splice junction of MxA exons 13 and 17.

In general, the primers provide for amplification of target nucleic acid to produce as target nucleic acid amplification product (also referred to as an "amplicon"). Primers may be used in connection with a probe. 5' primers generally bind to a region to provide for amplification of the target nucleic, and in some embodiments bind to a 5' portion of the target sequence. 3' primers generally bind to a sequence that is complementary to a 3' portion of the nucleic acid generated by extension from the 5' primer.

Primers or probes can be designed so as to have a sequence complementary to a sequence overlapping the splice junction of vMxA at exons 13 and 17. In some embodiments involving amplification-based detection, probes are designed so as to have a sequence complementary to a sequence flanked by the sequence(s) complementary to one or more primers used for amplification.

In some embodiments, the methods disclosed herein provide for detection and discrimination between MxA-encoding nucleic acid and vMxA-encoding nucleic acid, e.g. to allow for relative levels of MxA transcripts and vMxA transcripts to facilitate detection of the activity of a candidate agent in modulation of MxA splicing. For example, primers and probes for detection of MxA-encoding nucleic acid can provide for detection of a sequence overlapping a splice junction of exons 13 and 14, exons 16 and 17, or both. Alternatively, primers or probes can be designed which detect a nucleic acid transcript of the region deleted from vMxA (e.g., detection of exon 14, exon 15, or exon 16 nucleic acid).

Primers and probes can be readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

In some embodiments, the primer sequences are in the range of between 10-75 nucleotides in length, such as 10 to 70, 12 to 65, 15 to 60, 20 to 55, 25 to 50, 30 to 45, and the like. In some embodiments, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest.

An exemplary probe is in the range of between 10-50 nucleotides long, such as such as 10 to 50, 12 to 45, 15 to 40, 20 to 35, 25 to 30 and the like. In some embodiments, probes are in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest.

The probes may be coupled to labels for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. Exemplary materials for solid supports include controlled pore glass, glass plates, polystyrene, avidin-coated polystyrene beads, cellulose, nylon, acrylamide gel and activated dextran.

In some embodiments, the probe is attached to the solid support by a linker which serves to distance the probe from the solid support. The linker is usually at least 15-30 atoms in length, more preferably at least 15-50 atoms in length. The required length of the linker will depend on the particular solid support used. For example, a six atom linker is generally sufficient when high cross-linked polystyrene is used as the solid support. A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred.

In certain embodiments, an internal control (IC) is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

Interfering Nucleic Acid

The instant invention also provides interfering nucleic acids that interfere with production MxA and vMxA transcripts and production of vMxA protein. Interfering nucleic acids include small nucleic acid molecules, such as a short interfering nucleic acid (siNA), a short interfering RNA (siRNA), a double-stranded RNA (dsRNA), a micro-RNA (mRNA), and a short hairpin RNA (shRNA).

The terms "short interfering nucleic acid," "siNA," "short interfering RNA," "siRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner. Design of RNAi molecules when given a target gene are routine in the art. See also US 2005/0282188 (which is incorporated herein by reference) as well as references cited therein. See, e.g., Pushparaj et al. Clin Exp Pharmacol Physiol. 2006 May-Jun;33(5-6):504-10; Lutzelberger et al. Handb Exp Pharmacol. 2006; (173):243-59; Aronin et al. Gene Ther. 2006 Mar.; 13(6):509-16; Xie et al. Drug Discov Today. 2006 Jan.; 11 (1-2):67-73; Grunweller et al. Curr Med. Chem. 2005;12(26):3143-61; and Pekaraik et al. Brain Res Bull. 2005 Dec. 15;68(1-2):115-20. Epub 2005 Sep. 9.

Methods for design and production of siRNAs to a desired target are known in the art, and their application to MxA genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Non limiting examples of target sites for design of siNA molecules include the sequences designated m1, m2, m3, m4, m5, and m6 in FIG. 16, shown in bold and underlining. For example, suitable target sites for design of siNA include, but are not limited to: 1) 5' ccatcggaatcttga cgaa (SEQ ID NO:9); 2) 5'-gagagagaa gatcttcttt (SEQ ID NO:10); 3) 5'-cagcga gct-catcaca cat (SEQ ID NO:11); 4) 5-'gttc ttcctgatag ataaa (SEQ ID NO:12); 5) 5'-cgacacga gttccacaaa t (SEQ ID NO:13); and 6) 5'-tcacagatg tttcgataaa (SEQ ID NO:14). Additional target sites can be readily identified using the tools available to the ordinarily skilled artisan as discussed above.

It should be understood that the sequences provided above are the target sequences of the mRNAs encoding the target gene, and that the siRNA oligonucleotides used would comprise a sequence complementary to the target.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (mRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of FBXW8, CUL1, and/or CUL7.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22,23,24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17,34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Vectors, Host cells and Protein Production

The invention also provides vectors (constructs) containing a vMxA polynucleotide or fragment thereof as described herein, host cells, and the production of polypeptides by recombinant techniques. The vector may be, for example, a plasmid, viral, or retroviral vector.

The polynucleotide can be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs can contain sites for transcription initiation, termination, and, in the transcribed region, a translation initiation site. In some embodiments, the polypeptide is modified to include an N-terminal methionine.

The vectors can include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

Host cells can be any suitable host cell, including bacterial, mammalian cells, and non-mammalian cells. Representative examples of host cells include, but are not limited to, bacterial cells, such as *E. coli*, fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986).

The polypeptides described herein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. As a non-limiting example, high performance liquid chromatography ("HPLC") is employed for purification.

vMxA Polypeptides vMxA polypeptides and fragments thereof that are unique to vMxA relative to MxA are also contemplated herein. For example, in the case of a vMxA polypeptide produced in a cell following infection by a DNA virus (e.g., following infection of a human cell by HSV), polypeptides comprising an amino acid sequence encoded by the nucleic acid sequence at the exon 13-17 splice junction as described above are specifically contemplated. For example, as illustrated in FIG. 10, the vMxA protein produced in HSV-infected cells contains the amino acid sequence QEGG at the splice junction. The sequence "QEGG" and the sequence "EGGQ" are unique to this vMxA protein relative to MxA protein. Thus the present disclosure includes polypeptides and polypeptide fragments of this vMxA which comprise at least an amino acid sequence defining this splice variant gene product as unique relative to the amino acid sequence encoded by the parent MxA transcript. The present disclosure also includes vMxA polypeptides and portions of a vMxA polypeptide that are not present in MxA.

In some embodiments, a vMxA polypeptide has a molecular weight of approximately 56 kDa (e.g., from about 50 kDa to about 60 kDa) as determined by SDS-PAGE, e.g., when produced in HSV-infected HEL cells. The actual molecular weight of a vMxA protein may vary, depending on various factors, e.g., the cell in which the vMxA protein is produced, post-translation modifications, and the like.

In some embodiments, a subject vMxA polypeptide comprises an amino acid sequence having at least about 75%, at least about 80%, at least about 85%, at least about 90%, at least about 95%, at least about 97%, at least about 98%, at least about 99%, or 100% amino acid sequence identity to a sequence of at least about 20, at least about 25, at least about 30, at least about 50, at least about 75, at least about 85, at least about 90, at least about 100, at least about 125, at least about 150, at least about 175, at least about 200, at least about 225, at least about 250, at least about 275, at least about 300, at least about 325, at least about 350, at least about 375, at least about 400, at least about 425, at least about 450, at least about 475, or at least about 500 contiguous amino acids of the vMxA amino acid sequence set forth in FIG. 13B (SEQ ID NO:4).

In some embodiments, a subject vMxA polypeptide comprises an amino acid sequence having at least about 75%, at least about 80%, at least about 85%, at least about 90%, at least about 95%, at least about 97%, at least about 98%, at least about 99%, or 100% amino acid sequence identity to the amino acid sequence of amino acids 425 to 508 of the vMxA amino acid sequence set forth in FIG. 13B (SEQ ID NO:4). The amino acid sequence of amino acids 425 to 508 of the vMxA as set forth in FIG. 13B is not present in the MxA protein (e.g., full-length MxA protein). In some embodiments, a subject vMxA polypeptide comprises from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 70 to about 75, from about 75 to about 80, or from about 80 to about 84 contiguous amino acids of the amino acid sequence of amino acids 425 to 508 of the vMxA amino acid sequence set forth in FIG. 13B (SEQ ID NO:4).

In some embodiments, a subject vMxA polypeptide is a fusion protein, where the fusion protein comprises a vMxA polypeptide and a fusion partner, e.g., a polypeptide other than vMxA. In some embodiments, the fusion partner is attached to the N-terminus of the vMxA protein, e.g., NH$_2$-fusion partner-vMxA-COOH. In other embodiments, the fusion partner is attached to the C-terminus of the vMxA protein, e.g., NH$_2$-vMxA-fusion partner-COOH. In other embodiments, the fusion partner is internal to the vMxA protein, e.g., NH$_2$—(vMxA)$_1$-fusion partner-(vMxA$_2$-COOH)$_2$, where vMxA$_1$ and vMxA$_2$ are N-terminal and C-terminal domains, respectively, of vMxA.

Suitable fusion partners include, but are not limited to, immunological tags such as epitope tags, including, but not limited to, hemagglutinin, FLAG, myc, and the like; proteins that provide for a detectable signal, including, but not limited to, fluorescent proteins, enzymes (e.g., β-galactosidase, luciferase, horse radish peroxidase, alkaline phosphatase, etc.), and the like; polypeptides that facilitate purification or isolation of the fusion protein, e.g., metal ion binding polypeptides such as 6His tags, glutathione-S-transferase, and the like; polypeptides that provide for subcellular localization; and polypeptides that provide for secretion from a cell. Fusion partners that provide for a detectable signal are also referred to as "reporters."

Suitable reporter fusion partners, particularly for positioning at the N- or C-terminus, especially the C-terminus, of vMxA, include, but are not limited to, luciferase (e.g., firefly luciferase and derivatives thereof; *Renilla* luciferase and derivatives thereof); β-galactosidase; chloramphenicol acetyl transferase; glutathione S transferase; a green fluorescent protein (GFP), including, but not limited to, a GFP derived from *Aequoria victoria* or a derivative thereof, a number of which are commercially available; a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; a truncated GFP as described in Li et al. (1997) *J. Biol. Chem.* 272:28545-28549; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; a red fluorescent protein; a yellow fluorescent protein; a Lumio™ tag (e.g., a peptide of the sequence Cys-Cys-Xaa-Xaa-Cys-Cys, where Xaa is any amino acid other than cysteine, e.g., where Xaa-Xaa is Pro-Gly, which peptide is specifically bound by a fluorescein derivative having two As(III) substituents, e.g., 4',5'-bis(1,3,2-dithioarsolan-2-yl)fluorescein; see, e.g., Griffin et al. (1998) *Science* 281:269; Griffin et al. (2000) *Methods Enzymol.* 327:565; and Adams et al. (2002) *J. Am. Chem. Soc.* 124:6063); and the like.

In some embodiments, a subject vMxA fusion protein comprises a vMxA protein comprising an amino acid sequence of amino acids 425 to 508 of the amino acid sequence set forth in FIG. 13B (SEQ ID NO:4) and a fusion partner. In some embodiments, a subject vMxA fusion protein comprises a vMxA protein comprising an amino acid sequence of amino acids 425 to 508 of the amino acid sequence set forth in FIG. 13B (SEQ ID NO:4), and a fusion partner, where the fusion partner provides for a detectable signal.

In general, the polypeptides of interest in the subject invention are provided in a non-naturally occurring environment, e.g. are separated from their naturally occurring environment. In certain embodiments, the subject protein is present in a composition that is enriched for the protein as compared to a cell or extract of a cell that naturally produces the protein.

Also within the scope of the invention are variants; variants of polypeptides include mutants, fragments, and fusions. Mutants can include 1 or more, 2 or more, 3 or more, 5 or more, etc. amino acid substitutions, additions or deletions, where the areas for such modifications can be determined by, for example, alignment of the polypeptide amino acid sequence with that of a sequences from homologs and identifying regions of conservation and variation.

Fragments of a vMxA polypeptide comprise at the an amino acid sequence unique to a vMxA and can be at least about 9 aa, at least about 15 aa, be at least about 10 aa to at least about 15 aa in length, at least about 20 aa to 30 aa, at least about 30 aa, at least about 40 aa, at least about 50 aa, at least about 75 aa, at least about 100 aa, at least about 125 aa or at least about 150 aa in length or longer. Further representative examples of vMxA polypeptide fragments (useful in, for example, as antigens for antibody production), include those comprising a unique amino acid sequence relative to MxA and having from about 10-20, 15-25, 30-50, 40-75, 50-100 amino acid residues in length.

Methods of making vMxA polypeptides can be accomplished using any of a variety of methods. For example a polynucleotide having a sequence encoding a vMxA polypeptide, which may be optionally operably linked to one or more exogenous sequences (e.g., to provide a fusion protein), can be inserted into an expression vector, introduced into a suitable host cell, and the host cell cultured under conditions suitable for expression of the encoded polypeptide. Accordingly, the polynucleotides may be used to produce polypeptides, and these polypeptides may be used to produce antibodies by known methods described above and below.

In some embodiments, vMxA polypeptides (and optionally MxA polypeptides) having a heterologous detectable domain are used in the methods of the invention. Where a vMxA-encoding polypeptide or MxA-encoding polypeptide is modified to include a heterologous detectable domain, the detectable domain can be positioned at any suitable position in the coding sequence, e.g., at the N-terminus or C-terminus of the polypeptide. The detectable domain can be flanked by one or more linkers, which can be for example, from about 5 to 15, from 10 to 15, usually from about 6 to 12 amino acids in length, and can be about 20 amino acids or more, and, where flanking the detectable domain, are selected independently as to length and sequence. Linkers should be selected so that they do not substantially affect splicing of MxA or nuclear translocation of vMxA. Where nuclear translocation is to be assessed, the detectable domain and linkers should lack a functional domain (e.g., a region relatively rich for positively or negatively charged amino acids) that may affect trafficking of the protein.

Any detectable domain known in the art is suitable for use in the polypeptides described herein. A suitable detectable domain will generally be one that can be expressed in a desired host cell and will readily provide a detectable signal that can be assessed qualitatively and/or quantitatively, and can be detected directly or indirectly. Exemplary detectable domains include fluorescent polypeptides, wherein the fluorescent polypeptides include, but are not limited to, yellow fluorescent protein (YFP), cyan fluorescent protein (CFP), GFP, mRFP, RFP (tdimer2), HCRED, and the like, or variants thereof (e.g., fluorescent proteins modified to provide for enhanced fluorescence or a shifted emission spectrum, e.g., enhanced YFP). Further suitable fluorescent polypeptides, as well as specific examples of those listed herein, are provided in the art and are well known. "Fluorescent polypeptide" or "fluorescent polypeptide domain" as used herein is thus meant to encompass wild-type and modified fluorescent polypeptides. Exemplary non-fluorescent detectable domains include immunodetectable epitopes, such as FLAG, His tags, and the like. It should be noted that where the detectable domain is an immunodetectable domain, detection generally involves permeabilizing the cells (e.g., fixing the cells or treating the cells with a detergent) and contacting the cells with a detectably labeled antibody that specifically binds the immunodetectable domain. Alternatively, binding of the anti-immunodetectable domain antibody can be accomplished using a secondary antibody that is detectably labeled.

In embodiments where both MxA and vMxA proteins are to be detected, the detectable domain may be selected so that the detectable domains of MxA and vMxA have detectably different signals, e.g., detectably distinct emission spectra to facilitate detection of a distinct signal from each of MxA and vMxA (e.g., through use of different filters in the imaging system).

Anti-vMxA Antibodies

The invention also contemplates antibodies that specifically bind vMxA, e.g., by binding to an epitope defined by an amino acid sequence unique to vMxA, as well as antibodies that specifically detect MxA over detection of vMxA, e.g., by binding to an epitope defined by an amino acid sequence present in MxA and not in vMxA, e.g., an amino acid sequence of the region encoded by exons 14-16.

Antibodies include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to molecules that contain an antigen binding site that immunospecifically binds an antigen, including Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from human or non-human origin, e.g., murine (e.g., mouse and rat), donkey, sheep, rabbit, goat, guinea pig, camel, horse, or chicken. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Antibodies of the present invention may also be described or specified in terms of their binding affinity to a polypeptide of the invention. Exemplary binding affinities include those with a dissociation constant or Kd less than $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, etc.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%. Antibody production methods are well known in the art.

In some embodiments, a subject antibody binds specifically to an epitope present in or generated by amino acids 425 to 508 of the vMxA amino acid sequence set forth in FIG. 13B (SEQ ID NO:4). For example, in some embodiments, a subject antibody binds specifically to an epitope present in or generated by a stretch of from about 4 to about 6, from about 6 to about 10, from about 10 to about 15, from about 15 to about 20, from about 20 to about 25, from about 25 to about 30, from about 30 to about 40, from about 40 to about 50, from about 50 to about 60, from about 60 to about 70, from about 70 to about 80, or from about 80 to about 84 contiguous amino acids of the amino acid sequence set forth in amino acids 425 to 508 of FIG. 13B (SEQ ID NO:4).

Methods of Detecting vMxA Nucleic Acid or vMxA Protein
Nucleic-Acid Based Detection Methods In one aspect, the disclosure provides DNA-based assays for detecting the effect of a candidate agent upon alternative splicing of the MxA gene. Detection may be done using a wide variety of methods.

In one embodiment, the methods involve producing cDNA from an RNA transcript encoding vMxA and/or an RNA transcript encoding MxA, and amplifying the cDNA to produce an amplification product. The primers and probes can be designed for specific amplification and detection of vMxA transcripts only. For example, detection of an exemplary vMxA RNA can be accomplished using primers and probes can be designed for specific amplification and detection of a target, sequence comprising the exon 13-17 splice junction.

Alternatively, the primers and probes can be designed for amplification and detection of both MxA and vMxA transcripts, such that the MxA amplification product and vMxA amplification product are distinguishable (e.g., by size or by use of a probe). For example, the method can use differently detectably labeled probes, where a probe having a first detectable label hybridizes to a target sequence of the exon 13-17 splice junction, the a second probe having a second detectable label hybridizes to a sequence of any of exons 14-16 in the MxA transcript. In this embodiment, vMxA transcript levels can be compared to MxA transcript levels (e.g., to assess a change in the ratio of vMxA to MxA). In the context of a screening assay to assess antiviral activity of a candidate agent, a decrease in the ratio of a vMxA transcript level to a MxA transcript level indicates the agent inhibits production of vMxA transcripts and has antiviral activity. Other variations will be readily apparent to the ordinarily skilled artisan upon reading the present disclosure.

An amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect vMxA and MxA transcripts as desired. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

The fluorogenic 5' nuclease assay, known as the TAQMAN™ assay (Perkin-Elmer) can also be applied to detecting amplification products according to the methods of the invention. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes described herein can be used in TAQMAN™ analyses to detect the presence of infection in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers.

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad.Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3'end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, detection of vMxA and MxA transcripts in accordance with the methods described herein can involve amplifying a target nucleotide sequence using a nucleic acid polymerase having 5' to 3' nuclease activity, one or more primers capable of hybridizing to the target sequence or its extension product, and an oligonucleotide probe capable of hybridizing to the target sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. In some embodiments, the reporter molecule is a fluorescein dye and the quencher molecule is a rhodamine dye.

Another method of detection involves use of target sequence-specific oligonucleotide probes, which contain a region of complementarity to a target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally involves the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

The oligonucleotide molecules of the present invention may also be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The target sequences described herein can also utilize branched DNA technologies. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

As is readily apparent, design of the assays described herein is subject to a great deal of variation, and many formats are known in the art. The above descriptions are merely provided as guidance and one of skill in the art can readily modify the described protocols, using techniques well known in the art.

Polypeptide-Based Detection Methods

In one embodiment, vMxA polypeptide is detected in the cell. Similar to analysis of vMxA transcripts as discussed above in the nucleic-acid based detection methods, polypeptide-based detection can involve detecting vMxA polypeptide levels, which can optionally be compared to MxA polypeptide levels (e.g., to assess a change in the ratio of vMxA to MxA). In the context of a screening assay to assess antiviral activity of a candidate agent, a decrease in the ratio of vMxA polypeptide level to MxA polypeptide level indicates the agent inhibits vMxA production and has antiviral activity.

Polypeptide-based detection can also be used to assess nuclear translocation of vMxA, e.g., to assess a pattern of vMxA distribution in the cell in response to a candidate agent. A "vMxA pattern" refers to the distribution of vMxA in the cell, e.g., cytoplasmic, nuclear, etc. The effect of a candidate agent can be assessed over different periods of time and/or using different concentrations of the agent. The polypeptides can be detected by virtue of a detectable label, by use of a detectably labeled antibody, and the like.

Other variations will be readily apparent to the ordinarily skilled artisan upon reading the present disclosure.

Polypeptide-based detection can be accomplished using any suitable microscopic method. In one embodiment, the vMxA protein is provided as a fusion protein comprising a detectable domain which is fluorescent. In another embodiment, an immunodetectable domain of vMxA and/or MxA is exploited, and detection accomplished using a labeled primary antibody that specifically binds the detectable domain of vMxA or specifically binds the detectable domain of MxA. Alternatively, the primary antibody can be unlabeled, and binding of primary antibody detected using a secondary labeled antibody. Variations on antibody-based detection systems are known in the art, and can be readily adapted to the invention, as will be apparent to the ordinarily skilled artisan.

Where the detectable domain of vMxA is fluorescent, detection can be accomplished in real time and in live cells, e.g., by video microscopy. Alternatively, vMxA can be detected in fixed cells. For example, cells expressing vMxA can be exposed to an agent or other stimulus for different time periods (e.g., at about 10 s, 20 s, 30 s, 60 s, 90 s, 120 s, 150 s, 180 s, or more, or on the order of several minutes to hours). At the end of the time periods, the cells can be fixed according to a suitable method known in the art (e.g., using a fixative such as paraformaldehye, methanol, or the like). The vMxA distribution pattern can then be detected by detection of the detectable domain.

Where the detectable domain is a fluorescent polypeptide, methods of measuring and/or monitoring fluorescence are well known in the art. Both qualitative assessments (positive/negative) and quantitative assessments (e.g., comparative degree of fluorescence) may be provided by the present methods. Brightness can be measured using any known method, including, but not limited to, visual screening, spectrophotometry, spectrofluorometry, fluorescent microscopy (e.g., confocal microscopy), etc. In some embodiments, monitoring of a fluorescent vMxA polypeptides includes the use of an automated imaging system such as an Axon ImageXpress 5000, which can optionally be equipped with a live cell imaging chamber. Other suitable imaging systems include, but are not limited to, BD Biosciences (Pathway HT); Cellomics (ArrayScan V); Amersham (IN Cell Analyzer 1000; IN Cell Analyzer 3000); Molecular Devices (Discovery-1, Discovery-TMA, ImageXpress), and the like. In general, the best quality images may be obtained by focusing the microscope at the bottom of the cell on a support (e.g., the bottom of the cell contained in a microtiter plate).

In embodiments involving use of fixed cells, the cells can be examined at any appropriate time after fixing, preferably at a time after fixing in which the detectable signal from the detectable domain of the vMxA (and optionally MxA) can be readily detected.

Screening Methods

The compositions described herein can be used in screening assays to facilitate identification of an agent (e.g., a gene product or small molecule compound) or other stimulus that modulates production of MxA and/or vMxA (e.g., modulates levels of a vMxA RNA, e.g., relative to levels of MxA RNA) and/or levels of vMxA protein (e.g., levels of vMxA protein relative to MxA protein) and/or a vMxA nuclear translocation in a cell (e.g., a mammalian cell, e.g., a human cell) exposed to or infected with a DNA virus (e.g., herpesviridae member). In embodiments of particular interest, the agents inhibit production of a vMxA protein and/or translocation of a vMxA to the cell nucleus, indicating that the agent disrupts DNA virus modulation of these host cell functions and inhibits viral replication.

The screening methods of particular interest are those that facilitate identification of an agent having antiviral activity against a DNA virus, such as a DNA virus of the herpesviridae family. In general, a candidate agent is contacted with a cell which is susceptible in the presence of a DNA virus, where "in the presence of a DNA virus" is meant to indicate the cell may be pre-infected, infected at the time of contacting with the candidate agent, or may be infected following exposure to the candidate agent (e.g., to assess the ability of the candidate agent to inhibit infection). The cell is, of course, normally susceptible to infection by the DNA virus in the absence of the candidate agent. The cell can be any cell susceptible to infection by the DNA virus against which the candidate agent is to be screened, which cells include mammalian cells (including human and non-human cells such as, rodents (e.g., mouse, rat), swine, and the like) and fish. Mammalian cells, particularly human cells are of particular interest.

Following incubation for a desired time, the effect of the candidate agent is assessed by detecting the presence or absence of an effect on one or more of: 1) levels of MxA and/or vMxA transcripts; 2) translocation of vMxA to the nucleus; and 3) production of vMxA protein. In general, a reduction in one or more of: 1) the level of vMxA transcript; 2) vMxA nuclear translocation; and 3) levels of vMxA protein indicates the agent has antiviral activity against the DNA virus.

Generally a plurality of assay mixtures is performed in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate agents are tested in parallel. By "large number" is at least 10 to 50, usually at least 100, and more usually at least 1000.

A variety of different candidate agents may be screened by the above methods. Candidate agents encompass numerous chemical classes, and are in some embodiments organic molecules, e.g., small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, or at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

A subject screening method as described in more detail below may be part of a multi-step screening process of evaluating candidate agents. In multi-step screening processes of the subject invention, a candidate compound or library of compounds is subjected to screening in an in vivo model, e.g. a mouse model, following screening in cells. In other embodiments, a pre in vivo screening step may be employed, in which the compound is first subjected to an in vitro screening assay for its potential as a therapeutic agent in the treatment of anti-DNA virus infections.

Detecting an Agent that Affects Production of vMxA Transcripts

Detection of the effect on MxA to vMxA splicing can be accomplished in a variety of ways, including detection of levels of a vMxA encoding nucleic acid transcript, detection of levels of a vMxA polypeptide, or detection of a ratio of vMxA to MxA (either as transcripts or polypeptides).

In one embodiment, the methods are carried out by culturing a cell that naturally expresses and/or is modified to express MxA and vMxA transcripts, and when infected with a DNA virus, vMxA protein. In some embodiments, the cell contains a reporter construct to facilitate detection of a splicing event (and/or detection of MxA and/or vMxA transcripts) by provided a synthetic target sequence for the splicing machinery, such that a splicing event that produces vMxA can be detected by production of a non-naturally-occurring gene product, the production of which can provide for modulation of a detectable signal (e.g., a reporter gene, such as a fluorescent protein). For example, detection of vMxA transcripts can be accomplished using a reporter construct comprising sequences encoding a donor splice site of MxA exon 13, an acceptor splice site of MxA exon 17; and a sequence heterologous to the donor splice site and/or acceptor splice site, where splicing of a transcript a the MxA exon 13 donor splice site and the exon 17 acceptor splice site modulates a detectable signal, e.g., due to deletion of a sequence (e.g., the heterologous sequence) positioned between the donor and acceptor splice sites, and/or by providing for expression of a reporter gene upon joining of the donor and acceptor splice sites.

The cell is cultured in the presence of the candidate agent before, at the same time, or after contacting the cell with a DNA virus. Notably, the cell used in the assay must be susceptible to infection by the DNA virus. If the candidate agent inhibits DNA virus infection and/or inhibits DNA viral replication in the host cell, then this will be reflected by an increase in vMxA (e.g., as detected by an increase in the ratio of vMxA to MxA), and/or by inhibition of nuclear transport of vMxA to the nucleus, as compared to a vMxA level and/or vMxA nuclear transport in the absence of the agent.

The assays can be conducted in live cells, e.g., in in vitro cell culture. Alternatively, after a time sufficient for capturing any effect of the candidate agent, the cells can be fixed, and vMxA detected. For example, the cells can be contacted with a candidate agent, and, after a desired time period, the cells fixed and the pattern of vMxA in the cell assessed. The use of fixed cells in the detection step can facilitate more accurately the effect of time and agent concentration upon vMxA localization in the cell.

Where fixed cells are used, the assays can take advantage of detection systems that are not as amenable to use in live cells, e.g., antibody-based detection systems. Also, use of fixed cells in the assays described herein make the assays very amenable to high throughput, since many different assays can be run in parallel and the results of those assays examined at a later time point.

In embodiments involving detecting of vMxA nuclear translocation, the host cell can comprise a nucleic acid sequence encoding a viMxA protein which is detectably labeled, e.g., a vMxA fusion protein that comprises a fluorescent polypeptide. For example, the construct can contain a nucleic acid encoding a MxA protein which is operably linked to, or modified to contain, a nucleic acid encoding a reporter polypeptide (e.g., a fluorescent polypeptide). Alternatively, nuclear translocation of vMxA can be detected by exposing the cell to the candidate agent and DNA virus, and detecting vMxA protein (and, optionally, MxA) using an antibody, which may be detectably labeled.

Candidate agents of interest thus include those that, for example, decrease vMxA transcript levels or decrease vMxA nuclear translocation (as measured either qualitatively or quantitatively) by at least about 10%, at least about 15%, at least about 20%, at least about 25%, at least about 50%, at least about 100%, or at least 2-fold, at least about 5-fold, or at least about 10-fold or more when compared to a suitable control (e.g., relative to a level in the absence of the agent).

Detecting Agents that Affect Production of vMxA Protein

In some embodiments, a subject screening method is designed to detect agents that reduce production of vMxA protein in a cell, e.g., the level of vMxA in the cell is reduced. The methods generally involve contacting a test cell with a test agent, and determining the effect, if any, of the test agent on the level of vMxA in the test cell. A test agent that reduces the level of vMxA in the test cell, compared to a control level in the absence of the test agent, by at least about 10%, at least about 20%, at least about 25%, at least about 30%, at least about 40%, at least about 50%, at least about 60%, at least about 70%, at least about 80%, or at least about 90%, or more, is considered a candidate anti-viral agent.

The test cell comprises a DNA virus genome that encodes products that direct production of vMxA protein. In some embodiments, the test cell is infected with a DNA virus, or comprises all or a portion of a DNA viral genome. The presence of the viral genome in the cell results in production of vMxA protein, as described above. The vMxA protein that is produced in the presence of the viral genome (or gene products encoded thereby) can be detected in any of a number of ways. In some embodiments, vMxA protein is detected using an antibody specific for vMxA protein, as described above. The vMxA protein can be detected using an immunohistological staining method. Alternatively, the vMxA protein can be detected in a cell lysate made from the test cell. An anti vMxA antibody can be detectably labeled, either directly or indirectly.

Figure 19:
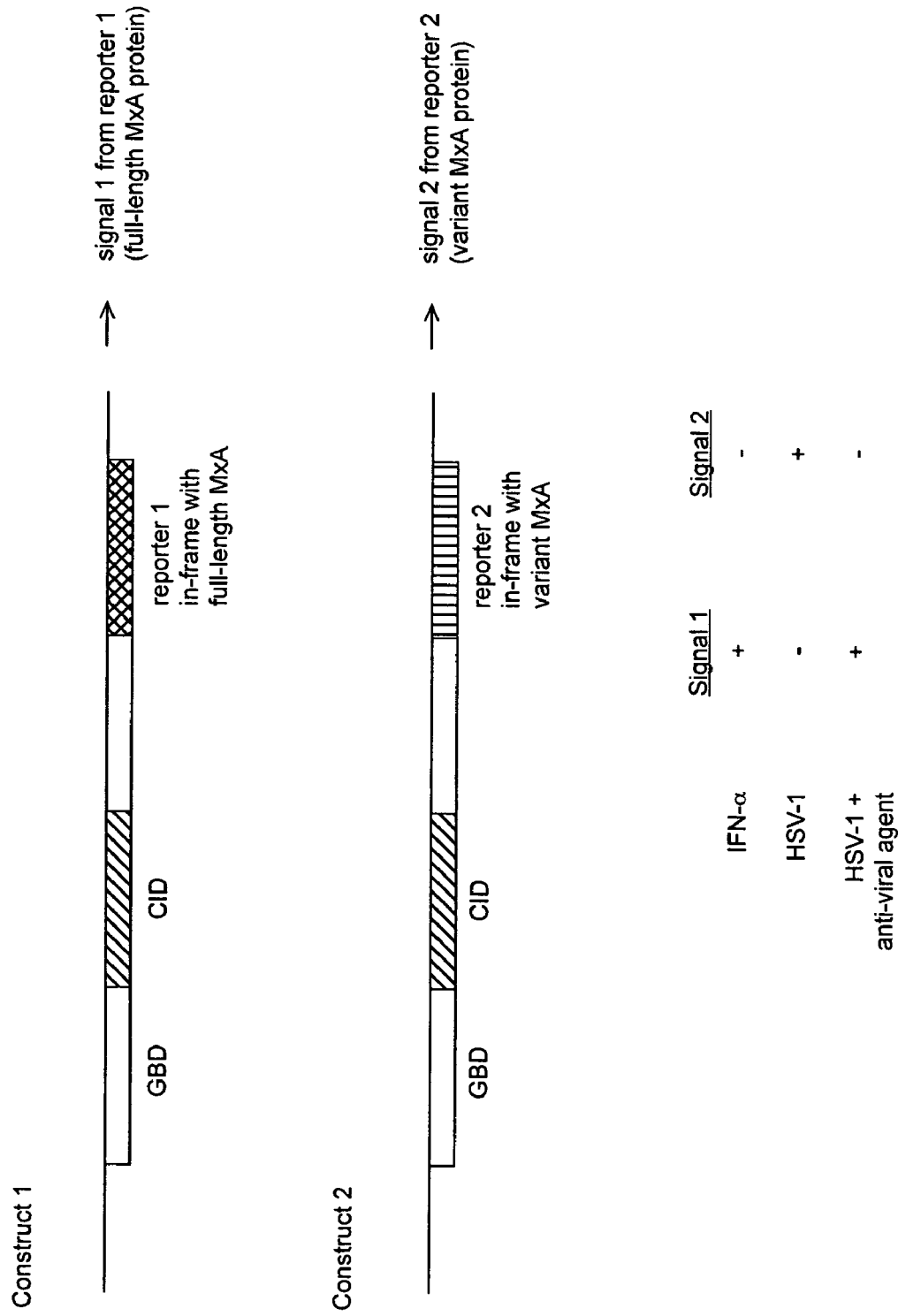
FIG. 19. An exemplary drug screening assay for identifying agents that reduce levels of variant MxA protein.

In some embodiments, the test cell comprises, in addition to a DNA viral genome, a first nucleic acid that comprises a nucleotide sequence encoding MxA RNA and a first reporter, where the first reporter is in frame with the MxA coding sequence; and a second nucleic acid that comprises a nucleotide sequence encoding MxA RNA, and a second reporter, where the second reporter is in frame with the vMxA coding sequence. A control cell comprises the first and second nucleic acids, but does not include the DNA viral genome. In the presence of DNA virus, the test cell produces more vMxA than MxA protein. Thus, in the presence of DNA virus the test cell produces a second signal from the second reporter, and less of a first signal from the first reporter. In some embodiments, the ratio of second signal (from the second reporter) to first signal (from the first reporter) is from about 10:1 to about 20:1, from about 20:1 to about 50:1, from about 50:1 to about 100:1, from about 100:1 to about 500:1, or from about 500:1 to about $10^3$:1, or higher. In some embodiments, the first signal from the first reporter is undetectable. An example of such an assay is illustrated schematically in FIG. 19.

The test cell is contacted in vitro with a test agent. A test agent that reduces production of vMxA protein will be detected by detecting a change in the ratio of first signal to second signal. An increase in the ratio of the first signal to second signal indicates that the test agent reduces production of vMxA protein. In some embodiments, the ratio of first signal to second signal in the presence of a test agent is from about 10:1 to about 20:1, from about 20:1 to about 50:1, from about 50:1 to about 100:1, from about 100:1 to about 500:1, or from about 500:1 to about $10^3$:1, or higher. Treatment of the control cell (e.g., the cell comprising the first and second nucleic acids, but not the DNA viral genome) with IFN-α also produces a ratio of first signal to second signal of from about 10:1 to about 20:1, from about 20:1 to about 50:1, from about 50:1 to about 100:1, from about 100:1 to about 500:1, or from about 500:1 to about $10^3$:1, or higher.

In a variation of the assay depicted in FIG. 19, the test cell comprises, in addition to a DNA viral genome, a first nucleic acid that comprises a nucleotide sequence encoding MxA RNA and a first reporter, where the first reporter is in frame with the MxA coding sequence; and a second nucleic acid that comprises a nucleotide sequence encoding vMxA RNA, and a second reporter, where the second reporter is in frame with the vMxA coding sequence. The assay is conducted as described above.

In other embodiments, the test cell comprises, in addition to a DNA viral genome, a first nucleic acid that comprises a nucleotide sequence encoding MxA RNA and a nucleotide sequence that encodes, as a first reporter, Cys-Cys-Xaa-Xaa-Cys-Cys (SEQ ID NO:15) embedded in a position within exons 14-16, such that the Cys-Cys-Xaa-Xaa-Cys-Cys (SEQ ID NO:15) coding sequence is in frame with the MxA coding sequence, where Xaa is any amino acid other than Cys (e.g., where Xaa-Xaa is Pro-Gly; and a second nucleic acid that comprises a nucleotide sequence encoding MxA RNA, and a second reporter, where the second reporter is in frame with the vMxA coding sequence. A control cell comprises the first and second nucleic acids, but does not include the DNA viral genome. In the presence of DNA virus, the test cell produces more vMxA than MxA protein. Thus, in the presence of DNA virus the test cell produces a second signal from the second reporter, and less of a first signal from the first reporter. In some embodiments, the ratio of second signal (from the second reporter) to first signal (from the first reporter) is from about 10:1 to about 20:1, from about 20:1 to about 50:1, from about 50:1 to about 100:1, from about 100:1 to about 500:1, or from about 500:1 to about $10^3$:1, or higher. In some embodiments, the first signal from the first reporter is undetectable. An example of such an assay is illustrated schematically in FIG. 20.

The (Cys-Cys-Xaa-Xaa-Cys-Cys; SEQ ID NO:15)-containing MxA protein is detected using a fluorescein derivative having two As(III) substituents, e.g., 4',5'-bis(1,3,2-dithioarsolan-2-yl)fluorescein; see, e.g., Griffin et al. (1998) Science 281:269; Griffin et al. (2000) *Methods Enzymol*. 327:565; and Adams et al. (2002) *J. Am. Chem. Soc*. 124:6063). Such compounds are available from, e.g., Invitrogen.

The test cell is contacted in vitro with a test agent. A test agent that reduces production of vMxA protein will be detected by detecting a change in the ratio of first signal to second signal. An increase in the ratio of the first signal to second signal indicates that the test agent reduces production of vMxA protein. In some embodiments, the ratio of first signal to second signal in the presence of a test agent is from about 10:1 to about 20:1, from about 20:1 to about 50:1, from about 50:1 to about 100:1, from about 100:1 to about 500:1, or from about 500:1 to about $10^3$:1, or higher. Treatment of the control cell (e.g., the cell comprising the first and second nucleic acids, but not the DNA viral genome) with IFN-α also produces a ratio of first signal to second signal of from about 10:1 to about 20:1, from about 20:1 to about 50:1, from about 50:1 to about 100:1, from about 100:1 to about 500:1, or from about 500:1 to about $10^3$:1, or higher.

In the above-described cell-based in vitro assays which employ MxA/reporter constructs, the first and second nucleic acids can be on the same construct, or on separate constructs. The first and second reporters are chosen such that they produce readily distinguishable signals.

Suitable reporters include, but are not limited to, a fluorescent protein, e.g., a green fluorescent protein, a red fluorescent protein, a yellow fluorescent protein, a blue fluorescent protein; a LUMIO™ tag; and the like.

Automated Screening Methods

The methods of the present invention may be automated to provide convenient, real time, high volume methods of screening compounds for antiviral activity against DNA viruses. Automated methods are designed to detect changes in the pattern of the detected signal (usually fluorescence) of a vMxA protein over time (i.e., comparing before and after exposure to a test sample), or by comparison to a control, which is not exposed to the test sample, or by comparison to pre-established indicia. Both qualitative assessments (positive/negative) and quantitative assessments (e.g., concentration of test sample required) may be provided by the present automated methods.

An embodiment of the present invention includes an apparatus for detecting changes in vMxA nuclear translocation to the methods described herein. This apparatus comprises means, such as a fluorescence measurement tool, for measuring change in a pattern of detectable signal of a detectably labeled vMxA in a eukaryotic cell in response to a particular candidate agent.

Measurement points may be over time, or among test and control samples. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool can be operatively coupled to a general purpose or application specific computer controller. The controller preferably comprises a computer program produced for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

MxA in Conferring Resistance to DNA Virus Infection

The invention also provides methods of rendering a human cell resistant to infection a DNA virus or inhibiting replication of a DNA virus in the cell by contacting a cell susceptible to DNA virus infection with an MxA protein or nucleic acid encoding an MxA protein so as to effect an increase in a level of cellular MxA protein in the cell in an amount effective to enhance resistance of the cell to DNA virus infection and/or to decrease replication of a DNA virus in the cell. Thus the invention provides methods for providing an antiviral effect by administering an agent other than an interferon.

This method finds particular application in treatment or prevention of a DNA virus infection, particularly a herpesvirus infection (e.g., HSV, VZV, etc.) in a mammal susceptible to infection by a DNA virus, particularly a human by administration of a therapeutically effective amount of an MxA protein and/or MxA-encoding nucleic acid. "Therapeutically effective amount" refers to a dose or dosage sufficient to provide for treatment for the disease state being treated or to otherwise provide the desired effect (e.g., an antiviral effect, with resistance to viral infection, inhibition of viral replication or both). The precise dosage will vary according to a variety of factors such as subject-dependent variables (e.g., age, immune system health, etc.), the disease (e.g., the species of the infecting pathogen), and the treatment being effected. "Treatment" or "treating" as used herein means any therapeutic intervention in a subject, usually a mammalian subject, generally a human subject, including: (i) prevention, that is, causing the clinical symptoms not to develop, e.g., preventing infection and/or preventing progression to a harmful state; (ii) inhibition, that is, arresting the development or further development of clinical symptoms, e.g., mitigating or completely inhibiting an active (ongoing) infection so that bacterial load is decreased to the degree that it is no longer seriously harmful, which decrease can include complete elimination of an infectious dose of a DNA virus from the subject; and/or (iii) relief, that is, causing the regression of clinical symptoms, e.g., causing a relief of fever, inflammation, and/or other symptoms caused by an infection.

A pharmaceutical composition can also contain a pharmaceutically acceptable carrier, which term refers to any pharmaceutical carrier that does not itself significantly or detectably induce an adverse effect, e.g., the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

Once formulated, the compositions contemplated by the invention can be administered to the subject by, for example, parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Administration of polynucleotide therapeutic composition agents includes local or systemic administration, including injection, oral administration, particle gun or catheterized administration, and topical administration. In general, the therapeutic polynucleotide composition contains an expression construct comprising a promoter operably linked to a polynucleotide encoding a MxA protein.

The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219, 740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell Biol.* (1994) 14:2411, and in Woffendin, *Proc. Natl. Acad. Sci.* (1994) 91:1581.

In some embodiments, an interfering nucleic acid is administered to an individual having a DNA virus infection, where the interfering nucleic acid reduces production of vMxA protein. Of particular interest are agents that a siNAs, as described above. Exemplary formulations and methods for the delivery of nucleic acid molecules are known in the art. For example, nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., PCT Publication Nos. WO 03/47518 and WO 03/46185), poly(lactic-co-glycolic)acid (PLGA) and PLCA microspheres (see for example U.S. Pat. No. 6,447,796 and U.S. Patent Application Publication No. U.S. Pat. No. 2,002,130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalacto-samine (PEI-PEG-triGAL) derivatives. In one embodiment, the nucleic acid molecules of the invention are formulated as described in U.S. Patent Application Publication No. 20030077829, incorporated by reference herein in its entirety.

In one embodiment, a siNA molecule is complexed with membrane disruptive agents such as those described in US 2001/0007666, incorporated by reference herein in its entirety. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety. In one embodiment, a siNA molecule is complexed with delivery systems as described in U.S. Pat. No. 2003/077829, WO 00/03683 and WO 02/087541, each incorporated herein by reference.

Alternatively, certain siNA molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45. Those skilled in the art realize that any nucleic acid can be expressed in eukaryotic cells from the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856.

Where the siNA is an RNA molecule, the siNA can be expressed from transcription units inserted into a vector. The recombinant vectors can be DNA plasmids, non-viral vectors or viral vectors. siNA expressing viral vectors can be constructed based on, but not limited to, adeno-associated virus, retrovirus, adenovirus, or alphavirus. The recombinant vectors capable of expressing the siNA molecules can be delivered as described above, and provide for transient or stable expression. For example, such vectors can include: 1) a transcription initiation region; 2) optionally, a transcription termination region; and 3) a nucleic acid sequence encoding at least one strand of an siNA molecule, wherein the sequence is operably linked to the initiation region and the termination region in a manner that allows expression and/or delivery of the siNA molecule.

Kits and Systems

Also provided by the subject invention are kits and systems that include the device of the invention for use in various applications, as described above. For example, the above-described assay reagents, including the cells, primers, probes, solid support with bound probes, reporter constructs as well as other detection reagents, can be provided in kits, with suitable instructions and other necessary reagents, in order to conduct the assays as described above. The kit will normally contain in separate containers the cells (e.g., recombinant cells), combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, digital versatile disk, VCR, CD-ROM, etc.) for carrying out the assay usually will be included in the kit. The kit can also contain, depending on the particular assay used, other packaged reagents and materials (i.e. wash buffers and the like). The kit can further contain a vial of a standard amount of a DNA virus for use in infecting the cells. Standard assays, such as those described above, can be conducted using these kits.

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided.

An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

EXAMPLES

Example 1

MxA Expressing Cells in IFN-α Treated Cell Monolayers are Resistant to VZV Infection (FIG. 1)

Primary human embryonic lung fibroblasts (HELs) were treated with IFN-α (10,000 U/ml) for 24 hours (hr), and subsequently infected with VZV. Specifically a confluent uninfected HEL monolyer ($1 \times 10^6$ cells) were co-cultured with $1 \times 10^5$ of heavily infected HEL cells. The cells were fixed in 2% PFA+0.2% Triton X-100, stained with anti-IE62 (red) and anti-MxA (green) or anti-gE (green) and anti-MxA(red) antibodies and analyzed by confocal microscopy (FIG. 1). Less than 5% of the cells were infected with VZV in IFN-α treated cells, based on IE62 expression. MxA expression was highly upregulated and localized to the cytoplasm in IE62 or gE negative cells.

Example 2

Figure 2A:
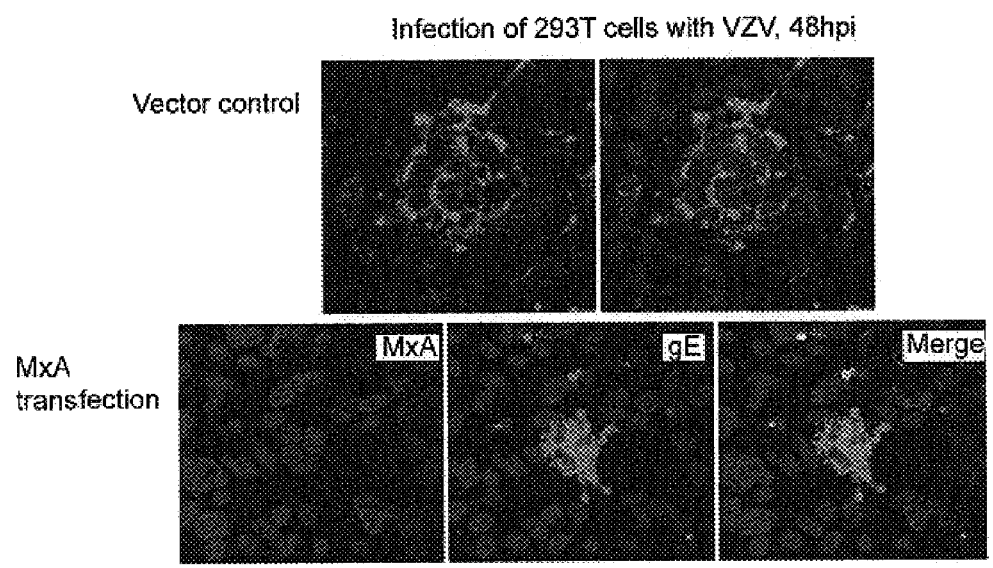
FIG. 2A. MxA overexpression reduces polykaryocyte formation in VZV infected 293T cells.
Figure 2B:
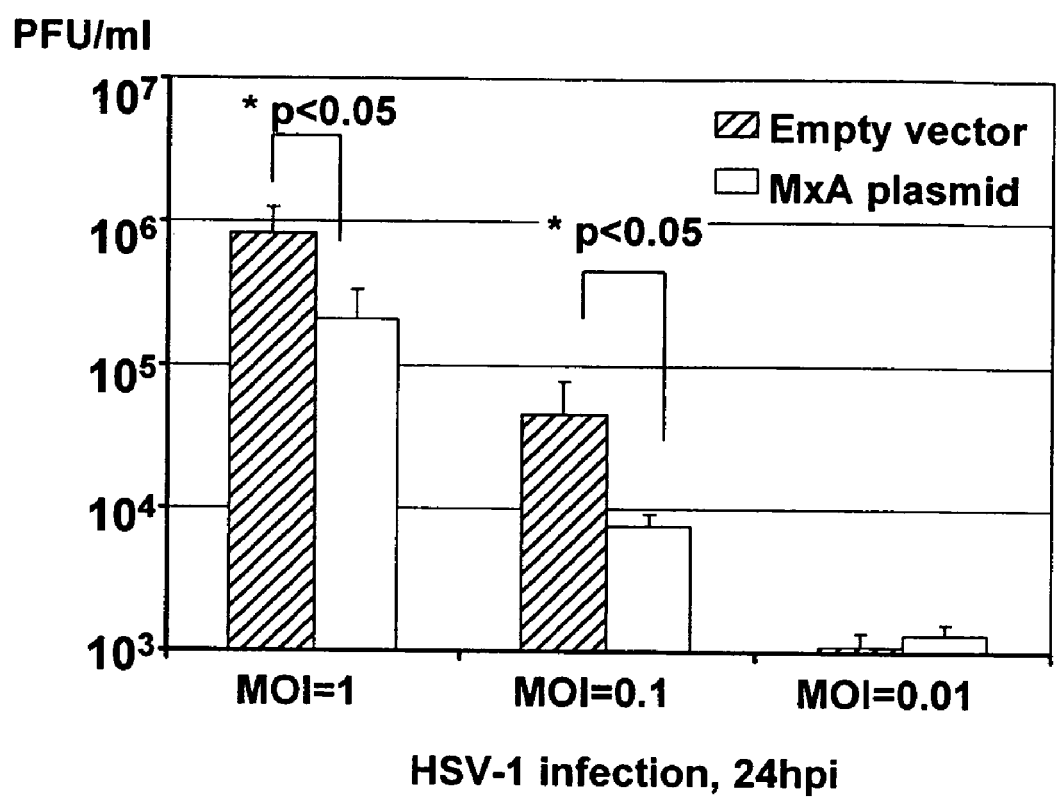
FIG. 2B. MxA reduces viral yield in HSV-1-infected cells.

MxA Overexpression Reduces Polykaryocyte Formation in VZV- or HSV-1-Infected 293T Cells (FIGS. 2A and 2B).

To examine whether MxA has functions in inhibiting VZV infection, 293T cells were transfected with a plasmid expressing MxA or empty vector and infected with VZV at 48 hours. Specifically $2 \times 10^5$ of 293T cells were co-cultured with $2 \times 10^4$ VZV infected HEL cells. Virus yields were measured by infectious focus assay in melanoma cells and the plaque size was evaluated by immunofluorescence based on polykaryocyte formation (FIG. 2A). Virus yields from MxA transfected and vector control were not different since 293T cells are not permissive for VZV infection. However, the size of VZV polykaryocyte formation in MxA transfected cells was significantly reduced as compared with vector control cells. The result suggested that MxA has the capacity to inhibit VZV cell-to-cell spread.

293T cells were transiently transfected with a plasmid expressing full-length MxA; and the cells were infected with HSV-1 at 48 hours, at a multiplicity of infection (MOI) of 0.01, 0.1, or 1. HSV-1 virus yields were measured using the infectious focus assay in melanoma cells. As shown in FIG. 2B, the results indicate that MxA inhibits production of virus.

Example 3

Figure 3:
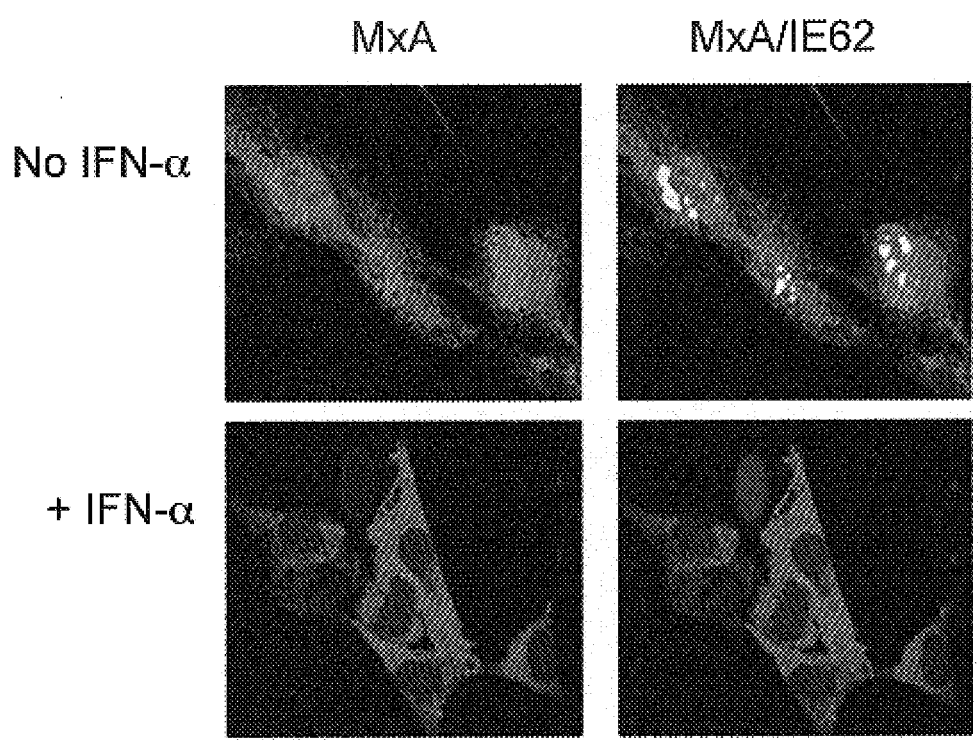
FIG. 3. MxA expression is induced in VZV rOka infected HEL cells.

MxA Expression is induced in VZV-infected HEL cells (FIG. 3)

HEL cells were infected with VZV rOka for 48 hr. Specifically, a confluent uninfected HEL monolayer ($1 \times 10^6$ cells) were co-cultured with $1 \times 10^5$ of heavily infected HEL cells and fixed and stained with anti-IE62 (red) and anti-MxA (green) antibodies and analyzed by confocal microscopy. Nuclear localization of IE62 is a marker of early VZV infection. At this stage of infection, the monolayer contains both VZV-infected and uninfected HEL cells. The results are shown in FIG. 3. In IE62 positive cells, MxA expression was upregulated significantly and was distributed throughout the cytoplasm in the granular pattern that was indistinguishable from that observed in IFN-α treated, uninfected HEL cells. However, in contrast to IFN-α treated, uninfected HEL cells, MxA expression was increased in the nuclei of early VZV-infected cells and colocalized with IE62 in a punctuate distribution as is characteristic of replication compartments.

Example 4

Figure 4:
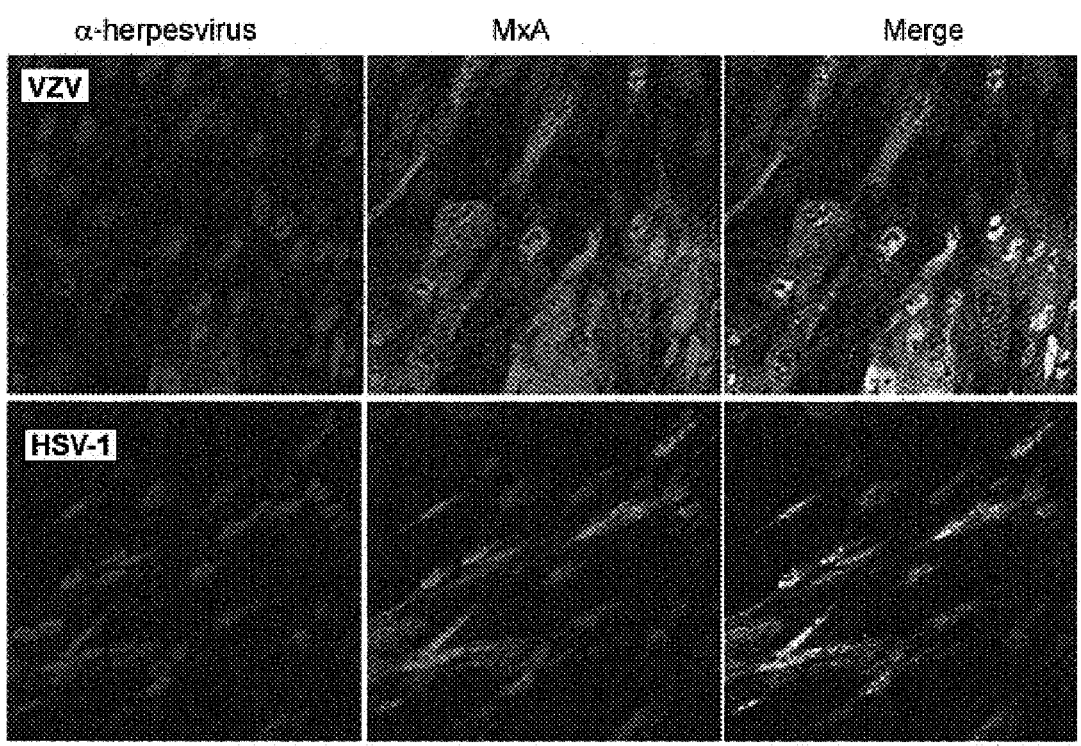
FIG. 4. Human alpha-herpesviral infection induces MxA expression and its nuclear translocation in fibroblasts.

Human Alpha-Herpesviral Infection Induces MxA Expression and its Nuclear Translocation in Fibroblasts (FIG. 4)

Fibroblast cells were infected with either VZV (by co-culture of a confluent uninfected HEL monolayer ($1 \times 10^6$ cells) with $1 \times 10^5$ of heavily infected HEL cells) or HSV-1 (at M.O.I.=0.1, one virus per 10 cells). After infection, MxA (green) and viral proteins (red) were analyzed by confocal microscopy as described above (FIG. 4). Both of these DNA viruses induced MxA expression and nuclear translocation.

Example 5

Figure 5:
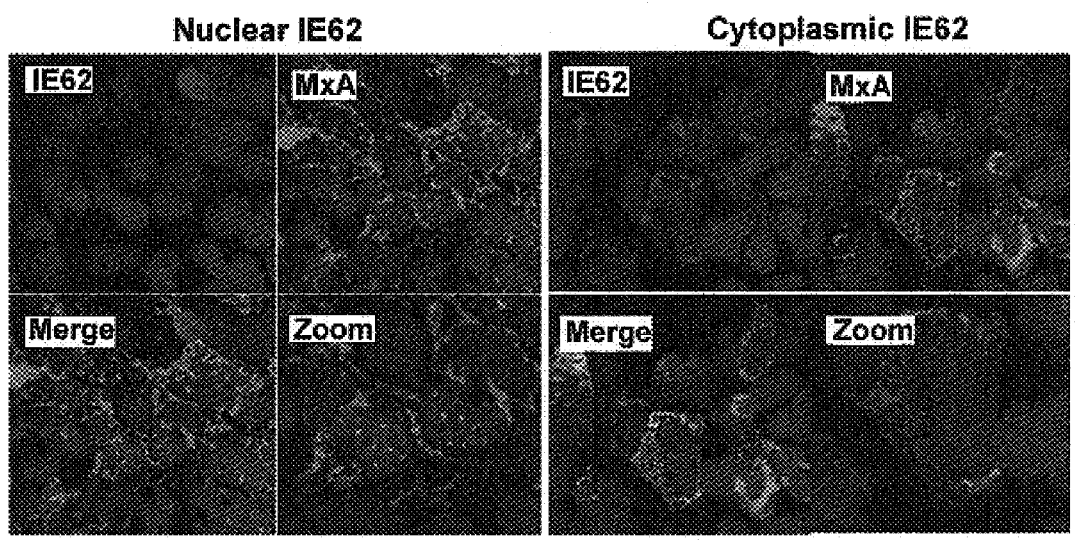
FIG. 5. VZV encoded protein IE62 is sufficient to mediate MxA nuclear translocation.

VZV Encoded Protein IE62 is Sufficient to Mediate MxA Nuclear Translocation (FIG. 5)

To examine whether overexpression of MxA might reveal nuclear translocation of MxA in the presence of IE62 and whether co-localization of MxA and IE62 to cell nuclei could be demonstrated under these conditions, 293T cells were cotransfected with MxA and IE62 and analyzed at 24 hours by confocal microscopy (FIG. 5). The expression of MxA in transfected cells exhibited the characteristic granular distribution in the cytoplasm (left panels). When MxA was overexpressed and cells were transfected with the IE62 plasmid, MxA was translocated to the nuclei of dual positive 293T cells. In the presence of IE62, and when MxA expression is upregulated, as it is in VZV-infected cells, MxA may bind to IE62 and be translocated to the nucleus because of the NLS in IE62 (FIG. 5, left panels). The results showed that IE62 directly interacted with MxA, as judged by co-localization and that MxA could translocate to the nuclei of 293T cells in the presence of IE62 without a requirement for other viral proteins. However, the co-localized MxA and IE62 proteins were distributed in a punctuate pattern throughout the nuclei and did not form the few larger focused areas consistent with replication compartments that were observed in VZV infected cells. When the cells were cotransfected with MxA and IE62 with a mutation in NLS which caused IE62 retention in the cytoplasm, the nuclear translocation of MxA was abolished (FIG. 5, right panels).

Example 6

Figure 6:
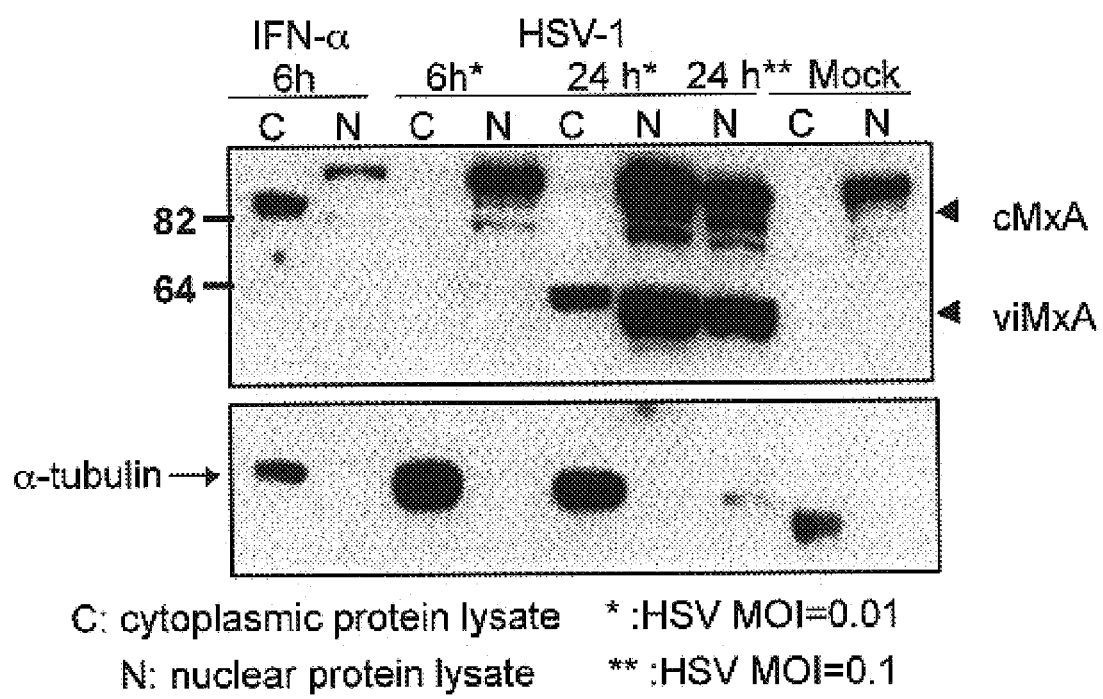
FIG. 6. HSV induced MxA protein is smaller in size than IFN-α induced MxA protein.

HSV Induced MxA Protein is Smaller in Size than IFN-Alpha Induced MxA Protein (FIG. 6)

Protein lysates from IFN-α treated, HSV infected and mock treated HEL cells were separated into cytoplasmic (C) and nuclear (N) fractions and subjected to 7.5% sodium dodecyl sulfate-polyacrylamide gel electrophoresis (SDS-PAGE)

and probed with anti-MxA antibody for Western blot analysis. The membrane was stripped and reprobed with anti-α-tubulin antibody as a cytoplasmic protein control. As is shown in FIG. 6, MxA was induced as early as 6 h after IFN-α treatment and restricted exclusively in the cytoplasmic fraction. MxA was also induced in HSV infected cells. However, the size of HSV induced MxA protein is smaller (about 56 KDa) than IFN-α induced MxA (about 76 KDa) and most of the protein was accumulated in the nuclear fraction.

Example 7

RT-PCR Analyses Reveals a Variant MxA Message in Virally Infected Cells (FIG. 7 and FIGS. 8A-C)

Figure 7:
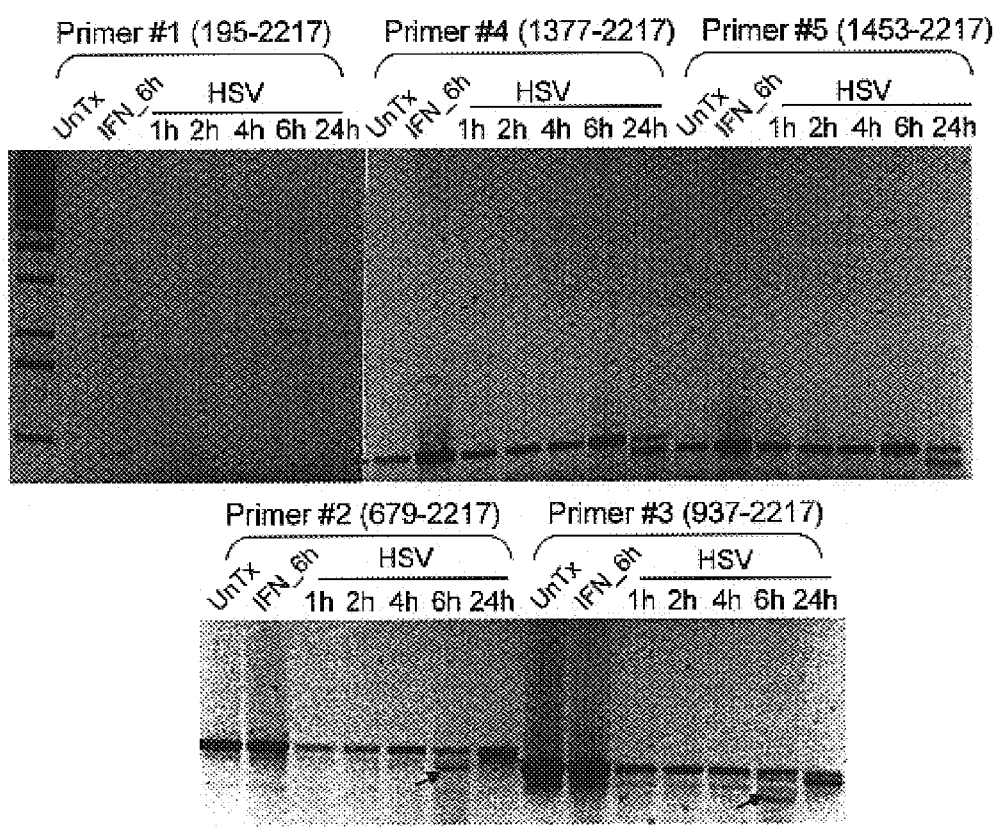
FIGS. 7 and 8A-C. RT-PCR analyses revealing a variant MxA message in virally infected cells.
Figure 8A:
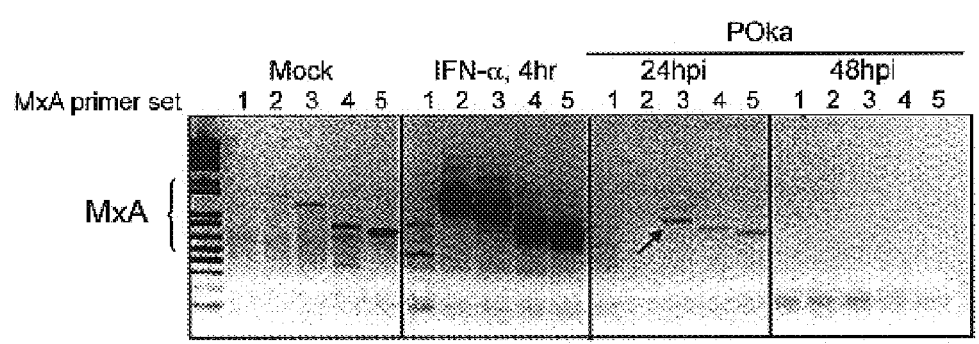
Figure 8B:
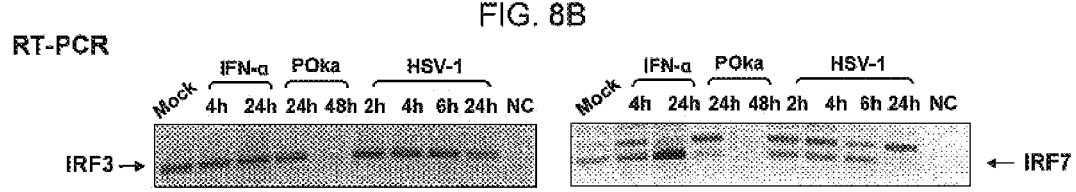

Total RNA was isolated from IFN-α treated, HSV-infected or mock infected HEL cells. The first strand cDNA was synthesized by random hexamer. MxA transcript was amplified by PCR using primer sets as indicated (see FIG. 11 for location of primers in MxA gene). Splice variants of MxA were detected in HSV infected samples collected at 6 h and 24 h but not in IFN-α treated or mock treated samples (FIG. 7, arrows). MxA splice variants were also detected in VZV infected cells (FIG. 8A; primer #3 set; arrow). IRF3 and IRF7 transcription are not activated in HSV and VZV infected cells (FIG. 8B).

Figure 8C:
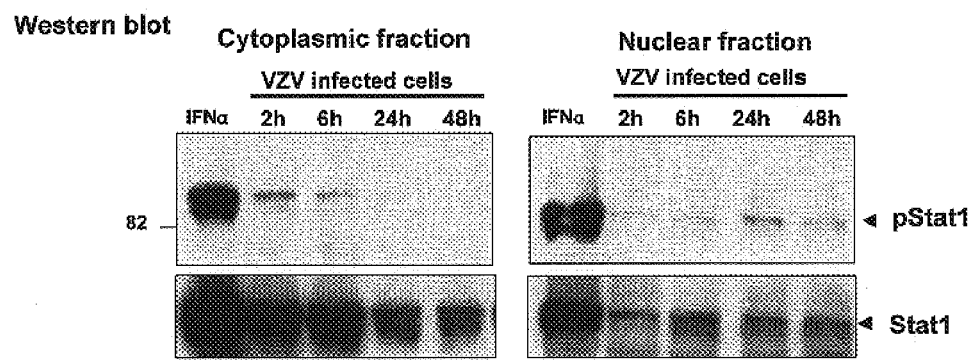

The IFN-α signaling pathway is not activated by VZV infection; and this lack of activation is due to failure of phosphorylation of Stat1. As shown in FIG. 8C, western blot analysis of the phosphorylation status of Stat1 shows that while phosphorylated Stat1 is present in IFN-α-treated cells, the amount of phosphorylated Stat1 is diminished in VZV infected cells, even though Stat1 is present in both cytoplasmic and nuclear fractions.

Example 8

Sequence Analysis of Variant MxA Message Demonstrates that it is a Splice Variant of MxA (FIGS. 9 and 10)

MxA splice variant from HSV 6 h RNA was subjected to PCR amplification with primers 3 and 82 (the primer set was designed to provide for amplification of a region from about nucleotide residue 937 to 2234 of Genbank accession number BC032602). Alignment of this sequence with MxA mRNA showed that the MxA variant is missing nucleotides 1563 to 2048 (boxed in FIG. 9A; nucleotides 642 to 1111 of the sequenced RT-PCR product; SEQ ID NO:6). This region corresponded to the central interactive domain of MxA which is known to have functions in the recognition of viral nucleocapsids and activation of GTPase activity. The coding sequence of the variant MxA transcript is provided in FIG. 9C (SEQ ID NO:7). The corresponding MxA and vMxA amino acid sequences are provided in FIGS. 10A-D. FIGS. 10A-D provides an MxA-encoding nucleotide sequence (SEQ ID NO: 16); a vMxA-encoding nucleotide sequence (SEQ ID NO: 17); an MxA amino acid sequence (SEQ ID NO: 18); and a vMxA amino acid sequence (SEQ ID NO:19). In FIGS. 10A-D, amino acid residues 372 and 540 of the full-length MxA protein are double underlined; these residues are the N-terminal and C-terminal residues of the central interaction domain.

FIG. 11, which is modified from FIG. 1 of Tazi-Ahnini et al. (2000) Human Genetics 106: 639-645, provides a schematic showing human MxA gene structure, RT-PCR primer binding sites and splice sites of MxA splice variant. Key: Human MxA gene organization: black boxes Exons (E); black lines introns (I); +1 transcription start site; left and right arrows indicate primer binding site and orientation. The vMxA splice variant is indicated (splice of exon 13 to exon 17).

Example 8

Figure 12A:
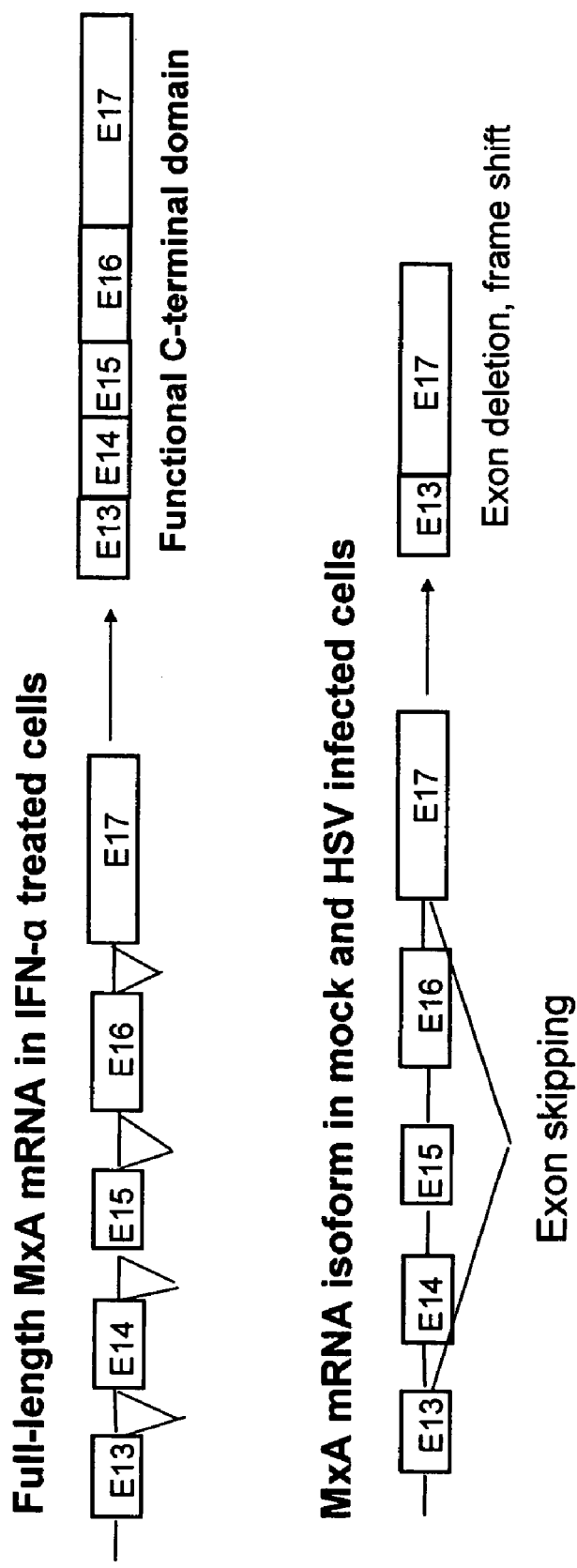
FIG. 12A. Schematic depiction of full-length MxA mRNA in IFN-α-treated cells, and variant MxA mRNA in mock- and HSV-infected cells.

Full-Length MxA Transcript and Variant MxA Transcripts in IFN-Alpha-Treated Cells and HSV-1-Infected Cells FIG. 12A is a schematic representation of full-length MxA mRNA in IFN-α-treated cells, and the MxA isoform ("variant MxA") mRNA present in mock-infected and HSV-infected cells. The transcripts are depicted from exon 13 (E13) on. As depicted in FIG. 12A, translation of the full-length MxA mRNA gives rise to a C-terminal domain that includes amino acid sequences encoded by exons 13-17. Translation of the variant MxA transcript gives rise to a protein that lacks amino acid sequences encoded by exons 14-16. Furthermore, the protein encoded by the variant MxA transcript has a different C-terminal amino acid sequence following the amino acid sequence encoded by exon 13, due to a frame shift.

Figure 12B:
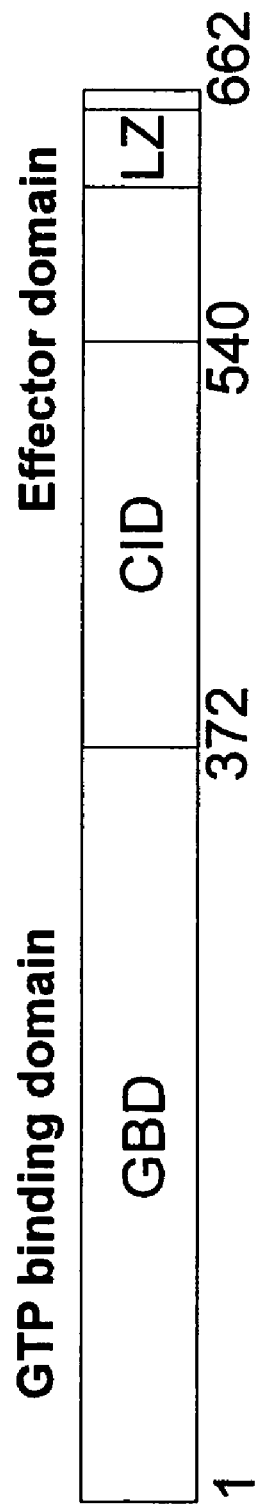
FIG. 12B. Schematic showing domain structure of full-length MxA protein.

The domain structure of full-length MxA protein is depicted schematically in FIG. 12B (adapted from Flohr et al. *FEBS Letters* 463:24-28), where the full-length MxA protein includes a GTP binding domain ("GBD") and an effector domain comprising a 169-amino acid central interaction domain ("CID") and a leucine zipper ("LZ"). The variant MxA protein lacks all but 53 amino acids of the CID, and does not include a LZ domain.

FIG. 13A provides the amino acid sequence of full-length MxA protein. FIG. 13B provides the amino acid sequence of variant MxA protein. Amino acid residues following exon 13-encoded residues are boxed.

Example 9

Production of Full-Length and Variant MxA Transcripts in Melanoma Cells

FIG. 14 depicts expression of MxA in melanoma cells. A monolayer of melanoma cells was transiently transfected with a plasmid expressing full-length MxA (left panel) or MxA splice variant (right panel). MxA (full-length, variant) expression was detected by immunofluorescence 48 hours after transfection.

Example 10

Figure 15A:
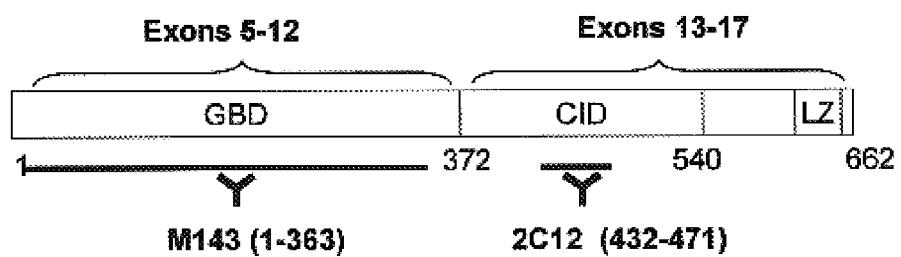
FIG. 15A. Schematic depiction of domain structure of full-length MxA protein, and regions to which monoclonal antibodies (MAb) M143 and 2C12 bind.
Figure 15B:
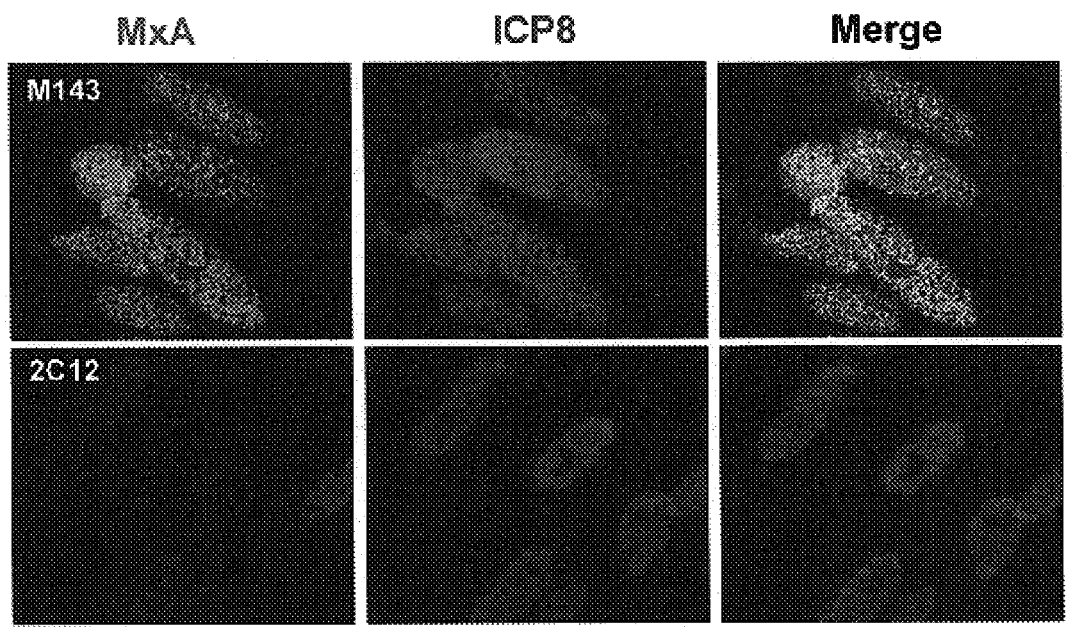
FIG. 15B. MAb M143 binds both full-length MxA and variant MxA proteins; MAb 2C12 binds full-length MxA protein, but not variant MxA protein.

Production of Full-Length and Variant MxA Protein in HSV-1-Infected Human Fibroblasts Human fibroblasts were infected with HSV-1 and stained with anti-MxA (M143 or 2C12) monoclonal antibody and anti-HSV ICP8 rabbit serum 24 hours post-infection. The monoclonal antibodies that recognize the N-terminal domain of MxA (M143) and an epitopes in the C-terminus of full-length MxA (2C12) are depicted schematically in FIG. 15A. FIG. 15B shows that the variant MxA protein that is made in HSV-1-infected cells binds M143, but not 2C12.

Example 11

MxA Knockdown by RNA Interference

Figure 17A:
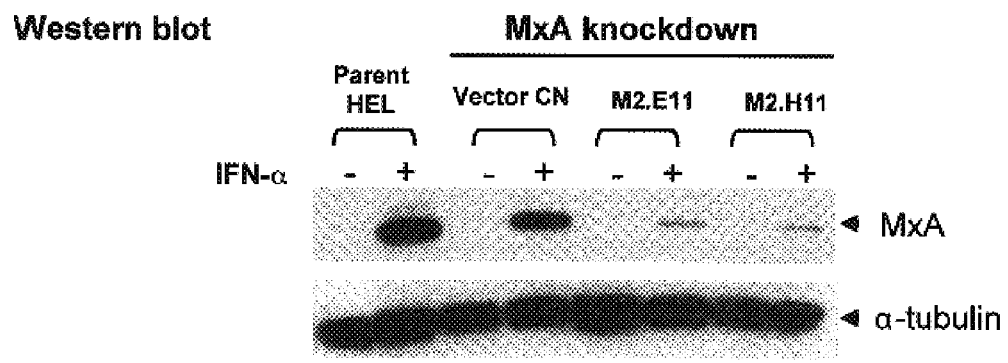
FIG. 17A. The level of MxA protein is significantly reduced in knockdown cell lines, as shown by Western blot.
Figure 17B:
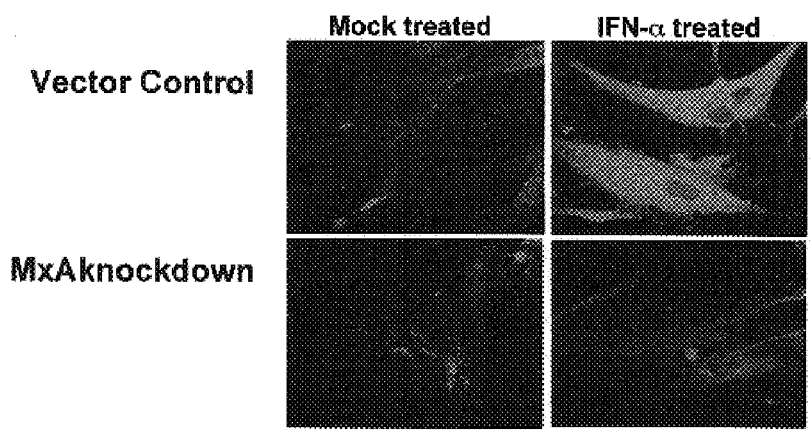
FIG. 17B. The level of MxA protein is significantly reduced in knockdown cell lines, as shown by immunofluorescence.

Human fibroblasts were infected with recombinant retrovirus that produces short hairpin RNA (shRNA) to inhibit MxA expression. Sequences encoding shRNA were cloned into the siRNA insertion site of the pSilencer 5.1-U6 Retro vector (Ambion). Target MxA sequences are depicted in FIG. 16. The MxA knockdown cell lines that were used were generated using the target sequence M2 (GTTCTTCCT-GATAGATAAA; SEQ ID NO:12). Infected cells were selected using puromycin and cloned into 96-well plates by limiting dilution. MxA knockdown was assessed by protein blot ("western" blot), as shown in FIG. 17A, and by immunofluorescence, as shown in FIG. 17B. Three clones that had reduced MxA expression were generated. MxA knockdown cells were infected with HSV-1 and evaluated by plaque assay at 24 hours post infection. As shown in FIG. 18, inhibition of MxA expression by siRNA reduced the yields of infections HSV-1 after infection at MOI of 1, 0.1, and 0.10 pfu/cell from all three clones of MxA knockdown cells.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. An isolated nucleic acid comprising:
   a) a nucleotide sequence encoding a deletion variant of MxA, wherein the MxA lacks a functional antiviral domain, wherein the nucleotide sequence comprises an MxA exon 13 contiguous with an MxA exon 17; or b) a complement of said nucleotide sequence.

2. An isolated nucleic acid comprising a nucleotide sequence encoding a vMxA polypeptide comprising amino acids 425 to 508 of the amino acid sequence set forth in SEQ ID NO:4.

3. The nucleic acid of claim 2, further comprising a nucleotide sequence encoding a polypeptide heterologous to the vMxA polypeptide, wherein said heterologous polypeptide-encoding sequence is in-frame with the vMxA-encoding sequence.

4. The nucleic acid of claim 3, wherein the heterologous polypeptide is selected from an epitope tag, a fluorescent protein, and an enzyme.

5. An isolated recombinant cell comprising the nucleic acid of claim 1 or claim 2.

6. The cell of claim 5, wherein said cell is a cultured animal cell.

7. A method of producing a vMxA polypeptide, comprising:
   culturing a recombinant cell of claim 5 in vitro under conditions suitable for expression of a vMxA polypeptide; and
   recovering the vMxA polypeptide.

8. The nucleic acid of claim 2, wherein the nucleic acid is a vector.

9. The nucleic acid of claim 2, wherein the nucleotide sequence is operably linked to a promoter.

10. The nucleic acid of claim 2, wherein said vMxA polypeptide has a length of 508 amino acids.

11. The nucleic acid of claim 2, wherein said vMxA polypeptide has a molecular weight of about 50 kDa to about 60 kDa.

12. The recombinant cell of claim 5, wherein said cell is a prokaryotic cell.

13. The recombinant cell of claim 5, wherein said cell is a eukaryotic cell.

* * * * *

UNITED STATES PATENT AND TRADEMARK OFFICE
CERTIFICATE OF CORRECTION

| | | |
|---|---|---|
| PATENT NO. | : 7,393,941 B2 | Page 1 of 1 |
| APPLICATION NO. | : 11/486901 | |
| DATED | : July 1, 2008 | |
| INVENTOR(S) | : Chia-Chi Ku | |

It is certified that error appears in the above-identified patent and that said Letters Patent is hereby corrected as shown below:

Col. 1, line 15-18

"This invention was made with government support under federal grant no. AI020459 awarded by the National Institutes of Health. The United States Government may have certain rights in this invention" should be replaced with -- This invention was made with government support under federal grant no. AI020459 awarded by the National Institutes of Health. The United States Government has certain rights in the invention. --

Signed and Sealed this

Eleventh Day of November, 2008

JON W. DUDAS
*Director of the United States Patent and Trademark Office*

```
                          SEQUENCE LISTING

<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: probe

<400> SEQUENCE: 1
tttcaagaag gaggccagca ag                                              22

<210> SEQ ID NO 2
<211> LENGTH: 10
<212> TYPE: PRT
<213> ORGANISM: Artificial Sequence
<220> FEATURE:
<223> OTHER INFORMATION: fragment derived from human source

<400> SEQUENCE: 2

Asn Asn Phe Gln Glu Gly Gly Gln Gln Ala
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: fragment derived from human source

<400> SEQUENCE: 3

Asn Asn Phe Gln Glu Gly His Lys Ile Leu
 1               5                  10

<210> SEQ ID NO 4
<211> LENGTH: 508
```

```
<212> TYPE: PRT
<213> ORGANISM: Homo sapiens

<400> SEQUENCE: 4

Met Val Val Ser Glu Val Asp Ile Ala Lys Ala Asp Pro Ala Ala Ala
 1               5                   10                  15

Ser His Pro Leu Leu Asn Gly Asp Ala Thr Val Ala Gln Lys Asn
            20                  25                  30

Pro Gly Ser Val Ala Glu Asn Leu Cys Ser Gln Tyr Glu Glu Lys
        35                  40                  45

Val Arg Pro Cys Ile Asp Leu Ile Asp Ser Leu Arg Ala Leu Gly Val
 50                  55                  60

Glu Gln Asp Leu Ala Leu Pro Ala Ile Ala Val Ile Gly Asp Gln Ser
 65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
                100                 105                 110

Lys Leu Val Asn Glu Asp Lys Trp Arg Gly Lys Val Ser Tyr Gln Asp
            115                 120                 125

Tyr Glu Ile Glu Ile Ser Asp Ala Ser Glu Val Glu Lys Glu Ile Asn
130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Pro Ser Asn Val Asp Ile Ala
210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Arg Asn Leu Val Phe His Leu Lys
            260                 265                 270

Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
            340                 345                 350

Ile Thr Glu Glu Leu Gln Lys Tyr Gly Val Asp Ile Pro Glu Asp Glu
        355                 360                 365

Asn Glu Lys Met Phe Phe Leu Ile Asp Lys Ile Asn Ala Phe Asn Gln
    370                 375                 380

Asp Ile Thr Ala Leu Met Gln Gly Glu Glu Thr Val Gly Glu Glu Asp
385                 390                 395                 400
```

```
Ile Arg Leu Phe Thr Arg Leu Arg His Glu Phe His Lys Trp Ser Thr
                405                 410                 415
Ile Ile Glu Asn Asn Phe Gln Glu Gly Gly Gln Gln Ala His Leu Gln
            420                 425                 430
Pro His Pro Phe Asp His Pro Val Leu His Ala Pro Asp Val Arg Pro
        435                 440                 445
Ala Ala Ser Glu Gly His Ala Ala Pro Ala Gly Gln Gly His Leu
    450                 455                 460
Gln Leu Ala Pro Glu Gly Ala Glu Arg His Gln Arg Gln Ala Glu Val
465                 470                 475                 480
Pro Glu Gly Ala Ala Cys Thr Ala Asp Ala Gly Ser Ala Pro Ala Cys
                485                 490                 495
Pro Val Pro Arg Leu Thr Thr Leu Cys Pro Ala Pro
                500                 505

<210> SEQ ID NO 5
<211> LENGTH: 662
<212> TYPE: PRT
<213> ORGANISM: Homo sapiens

<400> SEQUENCE: 5

Met Val Val Ser Glu Val Asp Ile Ala Lys Ala Asp Pro Ala Ala Ala
 1               5                  10                  15
Ser His Pro Leu Leu Asn Gly Asp Ala Thr Val Ala Gln Lys Asn
                20                  25                  30
Pro Gly Ser Val Ala Glu Asn Asn Leu Cys Ser Gln Tyr Glu Glu Lys
            35                  40                  45
Val Arg Pro Cys Ile Asp Leu Ile Asp Ser Leu Arg Ala Leu Gly Val
    50                  55                  60
Glu Gln Asp Leu Ala Leu Pro Ala Ile Ala Val Ile Gly Asp Gln Ser
65                  70                  75                  80
Ser Gly Lys Ser Ser Val Leu Glu Ala Leu Ser Gly Val Ala Leu Pro
                85                  90                  95
Arg Gly Ser Gly Ile Val Thr Arg Cys Pro Leu Val Leu Lys Leu Lys
                100                 105                 110
Lys Leu Val Asn Glu Asp Lys Trp Arg Gly Lys Val Ser Tyr Gln Asp
            115                 120                 125
Tyr Glu Ile Glu Ile Ser Asp Ala Ser Glu Val Glu Lys Glu Ile Asn
130                 135                 140
Lys Ala Gln Asn Ala Ile Ala Gly Glu Gly Met Gly Ile Ser His Glu
145                 150                 155                 160
Leu Ile Thr Leu Glu Ile Ser Ser Arg Asp Val Pro Asp Leu Thr Leu
                165                 170                 175
Ile Asp Leu Pro Gly Ile Thr Arg Val Ala Val Gly Asn Gln Pro Ala
            180                 185                 190
Asp Ile Gly Tyr Lys Ile Lys Thr Leu Ile Lys Lys Tyr Ile Gln Arg
        195                 200                 205
Gln Glu Thr Ile Ser Leu Val Val Pro Ser Asn Val Asp Ile Ala
    210                 215                 220
Thr Thr Glu Ala Leu Ser Met Ala Gln Glu Val Asp Pro Glu Gly Asp
225                 230                 235                 240
Arg Thr Ile Gly Ile Leu Thr Lys Pro Asp Leu Val Asp Lys Gly Thr
                245                 250                 255
Glu Asp Lys Val Val Asp Val Val Arg Asn Leu Val Phe His Leu Lys
```

-continued

```
                260                 265                 270
Lys Gly Tyr Met Ile Val Lys Cys Arg Gly Gln Gln Glu Ile Gln Asp
            275                 280                 285
Gln Leu Ser Leu Ser Glu Ala Leu Gln Arg Glu Lys Ile Phe Phe Glu
    290                 295                 300
Asn His Pro Tyr Phe Arg Asp Leu Leu Glu Glu Gly Lys Ala Thr Val
305                 310                 315                 320
Pro Cys Leu Ala Glu Lys Leu Thr Ser Glu Leu Ile Thr His Ile Cys
                325                 330                 335
Lys Ser Leu Pro Leu Leu Glu Asn Gln Ile Lys Glu Thr His Gln Arg
            340                 345                 350
Ile Thr Glu Glu Leu Gln Lys Tyr Gly Val Asp Ile Pro Glu Asp Glu
    355                 360                 365
Asn Glu Lys Met Phe Phe Leu Ile Asp Lys Ile Asn Ala Phe Asn Gln
370                 375                 380
Asp Ile Thr Ala Leu Met Gln Gly Glu Glu Thr Val Gly Glu Glu Asp
385                 390                 395                 400
Ile Arg Leu Phe Thr Arg Leu Arg His Glu Phe His Lys Trp Ser Thr
                405                 410                 415
Ile Ile Glu Asn Asn Phe Gln Glu Gly His Lys Ile Leu Ser Arg Lys
            420                 425                 430
Ile Gln Lys Phe Glu Asn Gln Tyr Arg Gly Arg Glu Leu Pro Gly Phe
    435                 440                 445
Val Asn Tyr Arg Thr Phe Glu Thr Ile Val Lys Gln Gln Ile Lys Ala
450                 455                 460
Leu Glu Glu Pro Ala Val Asp Met Leu His Thr Val Thr Asp Met Val
465                 470                 475                 480
Arg Leu Ala Phe Thr Asp Val Ser Ile Lys Asn Phe Glu Glu Phe Phe
                485                 490                 495
Asn Leu His Arg Thr Ala Lys Ser Lys Ile Glu Asp Ile Arg Ala Glu
            500                 505                 510
Gln Glu Arg Glu Gly Glu Lys Leu Ile Arg Leu His Phe Gln Met Glu
    515                 520                 525
Gln Ile Val Tyr Cys Gln Asp Gln Val Tyr Arg Gly Ala Leu Gln Lys
530                 535                 540
Val Arg Glu Lys Glu Leu Glu Glu Lys Lys Lys Ser Trp Asp
545                 550                 555                 560
Phe Gly Ala Phe Gln Ser Ser Ala Thr Asp Ser Ser Met Glu Glu
                565                 570                 575
Ile Phe Gln His Leu Met Ala Tyr His Gln Glu Ala Ser Lys Arg Ile
            580                 585                 590
Ser Ser His Ile Pro Leu Ile Ile Gln Phe Phe Met Leu Gln Thr Tyr
    595                 600                 605
Gly Gln Gln Leu Gln Lys Ala Met Leu Gln Leu Gln Asp Lys Asp
610                 615                 620
Thr Tyr Ser Trp Leu Leu Lys Glu Arg Ser Asp Thr Ser Asp Lys Arg
625                 630                 635                 640
Lys Phe Leu Lys Glu Arg Leu Ala Arg Leu Thr Gln Ala Arg Arg
                645                 650                 655
Leu Ala Gln Phe Pro Gly
            660
```

<210> SEQ ID NO 6

<211> LENGTH: 2753
<212> TYPE: DNA
<213> ORGANISM: Homo sapiens

<400> SEQUENCE: 6

```
ccacgcgtcc gcccagtgtc acggtggaca cgcctccctc gcgcccttgc cgcccacctg     60
ctcacccagc tcagggctt tggaattctg tggccacact gcgaggagat cggttctggg    120
tcggaggcta caggaagact cccactccct gaaatctgga gtgaagaacg ccgccatcca    180
gccaccattc aaggaggtg caggagaaca gctctgtgat accatttaac ttgttgacat    240
tacttttatt tgaaggaacg tatattagag cttactttgc aaagaaggaa gatggttgtt    300
tccgaagtgg acatcgcaaa agctgatcca gctgctgcat cccaccctct attactgaat    360
ggagatgcta ctgtggccca gaaaaatcca ggctcggtgg ctgagaacaa cctgtgcagc    420
cagtatgagg agaaggtgcg cccctgcatc gacctcattg actccctgcg ggctctaggt    480
gtggagcagg acctggccct gccagccatc gccgtcatcg ggaccagag ctcgggcaag    540
agctccgtgt tggaggcact gtcaggagtt gcccttccca gaggcagcgg atcgtgacc    600
agatgcccgc tggtgctgaa actgaagaaa cttgtgaacg aagataagtg gagaggcaag    660
gtcagttacc aggactacga gattgagatt tcggatgctt cagaggtaga aaaggaaatt    720
aataaagccc agaatgccat cgccggggaa ggaatgggaa tcagtcatga gctaatcacc    780
ctggagatca gctcccgaga tgtcccggat ctgactctaa tagaccttcc tggcataacc    840
agagtggctg tgggcaatca gcctgctgac attgggtata agatcaagac actcatcaag    900
aagtacatcc agaggcagga gacaatcagc ctggtggtgg tccccagtaa tgtggacatt    960
gccaccacag aggctctcag catggcccag gaggtggacc ccgagggaga caggaccatc   1020
ggaatcttga cgaagcctga tctggtggac aaaggaactg aagacaaggt tgtggacgtg   1080
gtgcggaacc tcgtgttcca cctgaagaag ggttacatga ttgtcaagtg ccggggccag   1140
caggagatcc aggaccagct gagcctgtcc gaagccctgc agagagagaa gatcttcttt   1200
gagaaccacc catatttcag ggatctgctg gaggaaggaa aggccacggt tccctgcctg   1260
gcagaaaaac ttaccagcga gctcatcaca catatctgta aatctctgcc cctgttagaa   1320
aatcaaatca aggagactca ccagagaata acagaggagc tacaaaagta tggtgtcgac   1380
ataccggaag acgaaaatga aaaatgttc ttcctgatag ataaaattaa tgcctttaat   1440
caggacatca ctgctctcat gcaaggagag gaaactgtag gggaggaaga cattcggctg   1500
tttaccagac tccgacacga gttccacaaa tggagtacaa taattgaaaa caattttcaa   1560
gaaggccata aaattttgag tagaaaaatc cagaaatttg aaaatcagta tcgtggtaga   1620
gagctgccag gctttgtgaa ttacaggaca tttgagacaa tcgtgaaaca gcaaatcaag   1680
gcactggaag agccggctgt ggatatgcta cacaccgtga cggatatggt ccggcttgct   1740
ttcacagatg tttcgataaa aaattttgaa gagtttttta acctccacag aaccgccaag   1800
tccaaaattg aagacattag agcagaacaa gagagagaag gtgagaagct gatccgcctc   1860
cacttccaga tggaacagat tgtctactgc caggaccagg tatacagggg tgcattgcag   1920
aaggtcagag agaaggagct ggaagaagaa aagaagaaga atcctgggga ttttggggct   1980
ttccaatcca gctcggcaac agactcttcc atggaggaga tctttcagca cctgatggcc   2040
tatcaccagg aggccagcaa gcgcatctcc agccacatcc ttgatcat ccagttcttc   2100
atgctccaga cgtacggcca gcagcttcag aaggccatgc tgcagctcct gcaggacaag   2160
gacacctaca gctggctcct gaaggagcgg agcgacacca gcgacaagcg gaagttcctg   2220
```

```
aaggagcggc ttgcacggct gacgcaggct cggcgccggc ttgcccagtt ccccggttaa   2280
ccacactctg tccagccccg tagacgtgca cgcacactgt ctgccccgt tcccgggtag    2340 ccactggact gacgacttga gtgctcagta gtcagactgg atagtccgtc tctgcttatc   2400
cgttagccgt ggtgatttag caggaagctg tgagagcagt ttggtttcta gcatgaagac   2460
agagccccac cctcagatgc acatgagctg gcgggattga aggatgctgt cttcgtactg   2520
ggaaagggat tttcagccct cagaatcgct ccaccttgca gctctcccct tctctgtatt   2580
cctagaaact gacacatgct gaacatcaca gcttatttcc tcatttttat aatgtccctt   2640
cacaaaccca gtgttttagg agcatgagtg ccgtgtgtgt gcgtcctgtc ggagccctgt   2700
ctcctctctc tgtaataaac tcatttctag cagacaaaaa aaaaaaaaaa aaa          2753

<210> SEQ ID NO 7
<211> LENGTH: 2268
<212> TYPE: DNA
<213> ORGANISM: Homo sapiens

<400> SEQUENCE: 7
ccacgcgtcc gcccagtgtc acggtggaca cgcctccctc gcgcccttgc cgcccacctg    60
ctcacccagc tcaggggctt tggaattctg tggccacact gcgaggagat cggttctggg   120
tcggaggcta caggaagact cccactccct gaaatctgga gtgaagaacg ccgccatcca   180
gccaccattc caaggaggtg caggagaaca gctctgtgat accatttaac ttgttgacat   240
tacttttatt tgaaggaacg tatattagag cttactttgc aaagaaggaa gatggttgtt   300
tccgaagtgg acatcgcaaa agctgatcca gctgctgcat cccaccctct attactgaat   360
ggagatgcta ctgtggccca gaaaatcca ggctcggtgg ctgagaacaa cctgtgcagc    420
cagtatgagg agaaggtgcg cccctgcatc gacctcattg actccctgcg ggctctaggt   480
gtggagcagg acctggccct gccagccatc gccgtcatcg ggaccagag ctcgggcaag    540 agctccgtgt tggaggcact gtcaggagtt gcccttccca gaggcagcgg gatcgtgacc   600
agatgcccgc tggtgctgaa actgaagaaa cttgtgaacg aagataagtg gagaggcaag   660
gtcagttacc aggactacga gattgagatt tcggatgctt cagaggtaga aaaggaaatt   720
aataaagccc agaatgccat cgccggggaa ggaatgggaa tcagtcatga gctaatcacc   780
ctggagatca gctcccgaga tgtcccggat ctgactctaa tagaccttcc tggcataacc   840
agagtggctg tgggcaatca gcctgctgac attgggtata agatcaagac actcatcaag   900
aagtacatcc agaggcagga gacaatcagc ctggtggtgg tccccagtaa tgtggacatt   960
gccaccacag aggctctcag catggcccag gaggtggacc ccgagggaga caggaccatc  1020
ggaatcttga cgaagcctga tctggtggac aaaggaactg aagacaaggt tgtggacgtg  1080
gtgcggaacc tcgtgttcca cctgaagaag ggttacatga ttgtcaagtg ccggggccag  1140
caggagatcc aggaccagct gagcctgtcc gaagccctgc agagagagaa gatcttcttt  1200
gagaaccacc catatttcag ggatctgctg gaggaaggaa aggccacggt tccctgcctg  1260
gcagaaaaac ttaccagcga gctcatcaca catatctgta aatctctgcc cctgttagaa  1320
aatcaaatca ggagactca ccagagaata acagaggagc tacaaaagta tggtgtcgac  1380
ataccggaag acgaaaatga aaaaatgttc ttcctgatag ataaaattaa tgcctttaat  1440
caggacatca ctgctctcat gcaaggagag gaaactgtag gggaggaaga cattcggctg  1500
tttaccagac tccgacacga gttccacaaa tggagtacaa taattgaaaa caattttcaa  1560
```

-continued

```
gaaggaggcc agcaagcgca tctccagcca catcccttg atcatccagt tcttcatgct    1620
ccagacgtac ggccagcagc ttcagaaggc catgctgcag ctcctgcagg acaaggacac    1680
ctacagctgg ctcctgaagg agcggagcga caccagcgac aagcggaagt tcctgaagga    1740
gcggcttgca cggctgacgc aggctcggcg ccggcttgcc cagttccccg gttaaccaca    1800
ctctgtccag ccccgtagac gtgcacgcac actgtctgcc cccgttcccg ggtagccact    1860
ggactgacga cttgagtgct cagtagtcag actggatagt ccgtctctgc ttatccgtta    1920
gccgtggtga tttagcagga agctgtgaga gcagtttggt ttctagcatg aagacagagc    1980
cccaccctca gatgcacatg agctggcggg attgaaggat gctgtcttcg tactgggaaa    2040
gggattttca gccctcagaa tcgctccacc ttgcagctct cccttctct gtattcctag     2100 aaactgacac atgctgaaca tcacagctta tttcctcatt tttataatgt cccttcacaa    2160
acccagtgtt ttaggagcat gagtgccgtg tgtgtgcgtc ctgtcggagc cctgtctcct    2220
ctctctgtaa taaactcatt tctagcagac aaaaaaaaaa aaaaaaaa                 2268
```

<210> SEQ ID NO 8
<211> LENGTH: 17
<212> TYPE: DNA
<213> ORGANISM: Artificial Sequence
<220> FEATURE:
<223> OTHER INFORMATION: probe

<400> SEQUENCE: 8
tttcaagaag gaggcca                                                    17

<210> SEQ ID NO 9
<211> LENGTH: 19
<212> TYPE: DNA
<213> ORGANISM: Artificial Sequence
<220> FEATURE:
<223> OTHER INFORMATION: target regions derived from human source

<400> SEQUENCE: 9
ccatcggaat cttgacgaa                                                  19

<210> SEQ ID NO 10
<211> LENGTH: 19
<212> TYPE: DNA
<213> ORGANISM: Artificial Sequence
<220> FEATURE:
<223> OTHER INFORMATION: target regions derived from human source

<400> SEQUENCE: 10
gagagagaag atcttctttt                                                 19

<210> SEQ ID NO 11
<211> LENGTH: 19
<212> TYPE: DNA
<213> ORGANISM: Artificial Sequence
<220> FEATURE:
<223> OTHER INFORMATION: target regions derived from human source

<400> SEQUENCE: 11
cagcgagctc atcacacat                                                  19

<210> SEQ ID NO 12
<211> LENGTH: 19
<212> TYPE: DNA
<213> ORGANISM: Artificial Sequence
<220> FEATURE:
<223> OTHER INFORMATION: target regions derived from human source -continued

```
<400> SEQUENCE: 12
gttcttcctg atagataaa                                                19

<210> SEQ ID NO 13
<211> LENGTH: 19
<212> TYPE: DNA
<213> ORGANISM: Artificial Sequence
<220> FEATURE:
<223> OTHER INFORMATION: target regions derived from human source

<400> SEQUENCE: 13
cgacacgagt tccacaaat                                                19

<210> SEQ ID NO 14
<211> LENGTH: 19
<212> TYPE: DNA
<213> ORGANISM: Artificial Sequence
<220> FEATURE:
<223> OTHER INFORMATION: target regions derived from human source

<400> SEQUENCE: 14
tcacagatgt ttcgataaa                                                19

<210> SEQ ID NO 15
<211> LENGTH: 6
<212> TYPE: PRT
<213> ORGANISM: Artificial Sequence
<220> FEATURE:
<223> OTHER INFORMATION: synthetic dye-binding tag sequences
<220> FEATURE:
<221> NAME/KEY: VARIANT
<222> LOCATION: (3)...(4)
<223> OTHER INFORMATION: Xaa = any amino acid other than Cysteine

<400> SEQUENCE: 15

Cys Cys Xaa Xaa Cys Cys
 1               5

<210> SEQ ID NO 16
<211> LENGTH: 1389
<212> TYPE: DNA
<213> ORGANISM: Homo sapiens

<400> SEQUENCE: 16
gtggtcccca gtaatgtgga cattgccacc acagaggctc tcagcatggc ccaggaggtg      60
gaccccgagg gagacaggac catcggaatc ttgacgaagc tgatctggt ggacaaagga      120 actgaagaca aggttgtgga cgtggtgcgg aacctcgtgt tccacctgaa gaagggttac     180
atgattgtca gtgccggggg ccagcaggag atccaggacc agctgagcct gtccgaagcc     240
ctgcagagag agaagatctt ctttgagaac cacccatatt tcagggatct gctggaggaa     300
ggaaaggcca cggttccctg cctggcagaa aaacttacca gcgagctcat cacacatatc     360
tgtaaatctc tgccccctgtt agaaaatcaa atcaaggaga ctcaccagag aataacagag     420
gagctacaaa agtatggtgt cgacataccg gaagacgaaa atgaaaaaat gttcttcctg     480
atagataaaa ttaatgccct taatcaggac atcactgctc tcatgcaagg agaggaaact     540
gtaggggagg aagacattcg gctgtttacc agactccgac acgagttcca caatggagt      600 acaataattg aaaacaattt tcaagaaggc cataaaattt tgagtagaaa aatccagaaa     660
tttgaaaatc agtatcgtgg tagagagctg ccaggctttg tgaattacag gacatttgag     720
acaatcgtga aacagcaaat caaggcactg gaagagccgg ctgtggatat gctacacacc     780
```

```
gtgacggata tggtccggct tgctttcaca gatgtttcga taaaaaattt tgaagagttt      840
tttaacctcc acagaaccgc caagtccaaa attgaagaca ttagagcaga acaagagaga      900
gaaggtgaga agctgatccg cctccacttc cagatggaac agattgtcta ctgccaggac      960
caggtataca ggggtgcatt gcagaaggtc agagagaagg agctggaaga agaaaagaag     1020
aagaaatcct gggattttgg ggcttttcaa tccagctcgg caacagactc ttccatggag     1080
gagatctttc agcacctgat ggcctatcac caggaggcca gcaagcgcat ctccagccac     1140 atcccttga tcatccagtt cttcatgctc cagacgtacg ccagcagct tcagaaggcc      1200 atgctgcagc tcctgcagga caaggacacc tacagctggc tcctgaagga gcggagcgac     1260
accagcgaca gcggaagtt cctgaaggag cggcttgcac ggctgacgca ggctcggcgc     1320
cggcttgccc agttccccgg ttaaccacac tctgtccagc cccgtagacg tgcacgcaca     1380
ctgtctgcc                                                            1389
```

<210> SEQ ID NO 17
<211> LENGTH: 942
<212> TYPE: DNA
<213> ORGANISM: Homo sapiens
<220> FEATURE:
<221> NAME/KEY: misc_feature
<222> LOCATION: 1, 3, 4, 5
<223> OTHER INFORMATION: n = A,T,C or G

<400> SEQUENCE: 17

```
ngnnnttagc attgattagc ggccgcgaat tcgcccttgt ggtccccagt aatgtggaca       60
tcgccaccac agaggctctc agcatggccc aggaggtgga ccccgaggga gacaggacca      120
tcggaatctt gacgaagcct gatctggtgg acaaaggaac tgaagacaag gttgtggacg      180
tggtgcggaa cctcgtgttc cacctgaaga agggttacat gattgtcaag tgccggggcc      240
agcaggagat ccaggaccag ctgagcctgt ccgaagccct gcagagagag aagatcttct      300
ttgagaacca cccatatttc agggatctgc tggaggaagg aaaggccacg gttccctgcc      360
tggcagaaaa acttaccagc gagctcatca cacatatctg taaatctctg cccctgttag      420
aaaatcaaat caaggagact caccagagaa taacagagga gctacaaaag tatggtgtcg      480
acataccgga agacgaaaat gaaaaaatgt tcttcctgat agataaaatt aatgccttta      540
atcaggacat cactgctctc atgcaaggag aggaaactgt aggggaggaa gacattcggc      600
tgtttaccag actccgacac gagttccaca aatggagtac aataattgaa aacaattttc      660
aagaaggagg ccagcaagcg catctccagc cacatccctt tgatcatcca gttcttcatg      720
ctccagacgt acggccagca gcttcagaag gccatgctgc agctcctgca ggacaaggac      780
acctacagct ggctcctgaa ggagcggagc gacaccagcg acaagcggaa gttcctgaag      840
gagcggcttg cacggctgac gcaggctcgg cgccggcttg cccagttccc cggttaacca      900
cactctgtcc agccccgtag acgtgcacgc acactgtctg cc                        942
```

<210> SEQ ID NO 18
<211> LENGTH: 446
<212> TYPE: PRT
<213> ORGANISM: Homo sapiens

<400> SEQUENCE: 18

```
Val Pro Ser Asn Val Asp Ile Ala Thr Thr Glu Ala Leu Ser Met Ala
 1               5                  10                  15
```

-continued

```
Gln Glu Val Asp Pro Glu Gly Asp Arg Thr Ile Gly Ile Leu Thr Lys
             20                  25                  30

Pro Asp Leu Val Asp Lys Gly Thr Glu Asp Lys Val Asp Val Val
         35                  40                  45

Arg Asn Leu Val Phe His Leu Lys Lys Gly Tyr Met Ile Val Lys Cys
             50                  55                  60

Arg Gly Gln Gln Glu Ile Gln Asp Gln Leu Ser Leu Ser Glu Ala Leu
 65                  70                  75                  80

Gln Arg Glu Lys Ile Phe Phe Glu Asn His Pro Tyr Phe Arg Asp Leu
                 85                  90                  95

Leu Glu Glu Gly Lys Ala Thr Val Pro Cys Leu Ala Glu Lys Leu Thr
                100                 105                 110

Ser Glu Leu Ile Thr His Ile Cys Lys Ser Leu Pro Leu Leu Glu Asn
             115                 120                 125

Gln Ile Lys Glu Thr His Gln Arg Ile Thr Glu Glu Leu Gln Lys Tyr
         130                 135                 140

Gly Val Asp Ile Pro Glu Asp Glu Asn Glu Lys Met Phe Phe Leu Ile
145                 150                 155                 160

Asp Lys Ile Asn Ala Phe Asn Gln Asp Ile Thr Ala Leu Met Gln Gly
                165                 170                 175

Glu Glu Thr Val Gly Glu Glu Asp Ile Arg Leu Phe Thr Arg Leu Arg
                180                 185                 190

His Glu Phe His Lys Trp Ser Thr Ile Ile Glu Asn Asn Phe Gln Glu
             195                 200                 205

Gly His Lys Ile Leu Ser Arg Lys Ile Gln Lys Phe Glu Asn Gln Tyr
         210                 215                 220

Arg Gly Arg Glu Leu Pro Gly Phe Val Asn Tyr Arg Thr Phe Glu Thr
225                 230                 235                 240

Ile Val Lys Gln Gln Ile Lys Ala Leu Glu Glu Pro Ala Val Asp Met
                245                 250                 255

Leu His Thr Val Thr Asp Met Val Arg Leu Ala Phe Thr Asp Val Ser
             260                 265                 270

Ile Lys Asn Phe Glu Glu Phe Phe Asn Leu His Arg Thr Ala Lys Ser
         275                 280                 285

Lys Ile Glu Asp Ile Arg Ala Glu Gln Glu Arg Glu Gly Glu Lys Leu
         290                 295                 300

Ile Arg Leu His Phe Gln Met Glu Gln Ile Val Tyr Cys Gln Asp Gln
305                 310                 315                 320

Val Tyr Arg Gly Ala Leu Gln Lys Val Arg Glu Lys Glu Leu Glu Glu
                325                 330                 335

Glu Lys Lys Lys Lys Ser Trp Asp Phe Gly Ala Phe Gln Ser Ser Ser
             340                 345                 350

Ala Thr Asp Ser Ser Met Glu Glu Ile Phe Gln His Leu Met Ala Tyr
         355                 360                 365

His Gln Glu Ala Ser Lys Arg Ile Ser Ser His Ile Pro Leu Ile Ile
         370                 375                 380

Gln Phe Phe Met Leu Gln Thr Tyr Gly Gln Gln Leu Gln Lys Ala Met
385                 390                 395                 400

Leu Gln Leu Leu Gln Asp Lys Asp Thr Tyr Ser Trp Leu Leu Lys Glu
                405                 410                 415
```

```
Arg Ser Asp Thr Ser Asp Lys Arg Lys Phe Leu Lys Glu Arg Leu Ala
            420                 425                 430

Arg Leu Thr Gln Ala Arg Arg Leu Ala Gln Phe Pro Gly
            435                 440                 445

<210> SEQ ID NO 19
<211> LENGTH: 292
<212> TYPE: PRT
<213> ORGANISM: Homo sapiens

<400> SEQUENCE: 19

Val Pro Ser Asn Val Asp Ile Ala Thr Thr Glu Ala Leu Ser Met Ala
 1               5                  10                  15

Gln Glu Val Asp Pro Glu Gly Asp Arg Thr Ile Gly Ile Leu Thr Lys
            20                  25                  30

Pro Asp Leu Val Asp Lys Gly Thr Glu Asp Lys Val Val Asp Val Val
            35                  40                  45

Arg Asn Leu Val Phe His Leu Lys Lys Gly Tyr Met Ile Val Lys Cys
 50                  55                  60

Arg Gly Gln Gln Glu Ile Gln Asp Gln Leu Ser Leu Ser Glu Ala Leu
 65                  70                  75                  80

Gln Arg Glu Lys Ile Phe Phe Glu Asn His Pro Tyr Phe Arg Asp Leu
                85                  90                  95

Leu Glu Glu Gly Lys Ala Thr Val Pro Cys Leu Ala Glu Lys Leu Thr
            100                 105                 110

Ser Glu Leu Ile Thr His Ile Cys Lys Ser Leu Pro Leu Leu Glu Asn
            115                 120                 125

Gln Ile Lys Glu Thr His Gln Arg Ile Thr Glu Glu Leu Gln Lys Tyr
            130                 135                 140

Gly Val Asp Ile Pro Glu Asp Glu Asn Glu Lys Met Phe Phe Leu Ile
145                 150                 155                 160

Asp Lys Ile Asn Ala Phe Asn Gln Asp Ile Thr Ala Leu Met Gln Gly
                165                 170                 175

Glu Glu Thr Val Gly Glu Glu Asp Ile Arg Leu Phe Thr Arg Leu Arg
            180                 185                 190

His Glu Phe His Lys Trp Ser Thr Ile Ile Glu Asn Asn Phe Gln Glu
            195                 200                 205

Gly Gly Gln Gln Ala His Leu Gln Pro His Pro Phe Asp His Pro Val
            210                 215                 220

Leu His Ala Pro Asp Val Arg Pro Ala Ala Ser Glu Gly His Ala Ala
225                 230                 235                 240

Ala Pro Ala Gly Gln Gly His Leu Gln Leu Ala Pro Glu Gly Ala Glu
                245                 250                 255

Arg His Gln Arg Gln Ala Glu Val Pro Glu Gly Ala Ala Cys Thr Ala
            260                 265                 270

Asp Ala Gly Ser Ala Pro Ala Cys Pro Val Pro Arg Leu Thr Thr Leu
            275                 280                 285

Cys Pro Ala Pro
            290
```